(12) United States Patent
Cahoon et al.

(10) Patent No.: US 6,762,345 B1
(45) Date of Patent: Jul. 13, 2004

(54) PLANT STEAROYL DESATURASES

(75) Inventors: Rebecca E. Cahoon, Wilmington, DE (US); Omolayo O. Famodu, Newark, DE (US); Jennie Bih-Jien Shen, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/452,937

(22) Filed: Dec. 2, 1999

Related U.S. Application Data

(60) Provisional application No. 60/110,785, filed on Dec. 3, 1998.

(51) Int. Cl.$^7$ .............................. A01H 5/00; C12N 5/04; C12N 15/82
(52) U.S. Cl. ...................... 800/281; 800/298; 435/69.1; 435/419; 435/468; 536/23.6
(58) Field of Search ....................... 536/23.6; 435/69.1, 435/468, 419; 800/281, 298

(56) References Cited

PUBLICATIONS

National Center for Biotechnology Information General Identifier No. 976257, Feb. 8, 1999, H. Akagi et al., Nucleotide sequence of a Stearoyl–Acyl Carrier Protein Desaturase cDNA from Developing Seeds of Rice.
Myeon H. Cho et al., Plant Phys., vol. 108(2):845–846 (1995), The Effects of Mastoparan on the Carrot Cell Plasma Membrane Polyphosphoinositide Phospholipase C1.
National Center for Biotechnology Information General Identifier No. 1020096, Apr. 14, 2000, Y. Yukawa et al., Structure and Expression of Two cDNA Clones encoding Stearoyl–Acyl Carrier Protein Desaturase in Sesame.
National Center for Biotechnology Information General Identifier No. 134944, Feb. 15, 2000, G. A. Thompson et al., Primary Structures of the Precursor and Mature Forms of Stearoyl–Acyl Carrier Protein Desaturase from Safflower Embryos and Requirement of Ferredoxin for Enzyme Activity.
Gregory A. Thompson et al., PNAS, vol. 88(6):2578–2582 (1991), Primary Structures of the Precursor and Mature Forms of Stearoyl–Acyl Carrier Protein Desaturase from Safflower Embryos and Requirement of Ferredoxin for Enzyme Activity.
National Center for Biotechnology Information General Identifier No. 3915029, Feb. 15, 2000, H. Akagi et al., Nucleotide Sequence of a Stearoyl–Acyl Carrier Protein Desaturase cDNA from Developing Seeds of Rice.
National Center for Biotechnology Information General Identifier No. 575942, Feb. 1, 2000, Y. Yukawa et al., Structure and Expression of Two Seed–Specific cDNA Clones encoding Stearoyl–Acyl Carrier Protein Desaturase from Sesame, Sesamum Indicum L.
Yasushi Yukawa et al., Plant Cell Phys., vol. 37(2):201–205 (1996), Structure and Expression of Two Seed–Specific cDNA Clones encoding Stearoyl–Acyl Carrier Protein Desaturase from Sesame, Sesamum Indicum L.
National Center for Biotechnology Information General Identifier No. 3915030, Feb. 15, 2000, M. Trucci et al.
National Center for Biotechnology Information General Identifier No. 2970034, Feb. 7, 1999, M. Mizutani–Fukuchi et al., Characterization of Delta 9 Acyl–Lipid Desaturase Homologues from Arabidopsis Thaliana.
Masako Fukuchi–Mizutani et al., Plant Cell Phys., vol. 39(2):247–253, (1998), Characterization of Delta 9 Acyl–Lipid Desaturase Homologues from Arabidopsis Thaliana.
Ann Owens Merlo et al., (1998) Plant Cell 10:1603–1621, Ribozymes Targeted to Stearoyl–ACP Delta 9 Desaturase mRNA Produce Heritable Increases of Stearic Acid in Transgenic Maize Leaves.
Ulf Diczfalusy et al., (1995) Biochim. Biophys. Acta 1259:313–316, Clofibrate Treatment Increases Stearoyl-–CoA Desaturase mRNA Level and Enzyme Activity in Mouse Liver.

*Primary Examiner*—Elizabeth F. McElwain

(57) ABSTRACT

This invention relates to an isolated nucleic acid fragment encoding a stearoyl desaturases. The invention also relates to the construction of a chimeric gene encoding all or a portion of the stearoyl desaturases, in sense or antisense orientation, wherein expression of the chimeric gene results in production of altered levels of the stearoyl desaturases in a transformed host cell.

15 Claims, 5 Drawing Sheets

STEAROYL-ACP DESATURASE ALIGNMENT

```
corn (SIN 14)         MALRASPVSHGTAAAPLPPFARRRMARGVVVAMASTINR-----VKTVKEPYTPPREVHR
rice (SIN 20)         MAFAASHTASPSSCGGVAQ--RRSNGMSPVVAMASTINR-----VKTAKKPYTPPREVHL
wheat (SIN 20)        ------------------------------------------------------------
gi_3915029            MAFAASHTASPYSCGGVAQ--RRSNGMSKMVAMASTINR-----VKTAKKPYTPPREVHL
prickly poppy (SIN 16) MALKLNPLTFQSQKFPCFGFPNVANVRSPKVFMASTLRSSSSKETEKLKKPFTPPREVHV
gi_575942             MALKLNAINFQSPKCPSFAIPPVASVRSPKFMASTLRSGS-KEVETVKRPFNPPREVHV
prickly poppy (SIN 18) HQI-----------------------------------------------PSSSPKKINQ
gi_3915030            MALNFNSPTFQSIKT---TRRPCSPLRSPRVFMASTLRP-PSVEDGNVKKPFSPPREVHV corn (SIN 14)         QITHSLPPQKREIFDSLQPWAKDNLLNLLKPVEKSWQPQDFLPEPSSDGFYDEVKELRER
rice (SIN 20)         QVKHSLPPQKREIFDSLQPWAKENLLNLLKPVEKSWQPQDFLPDPSSDGFYDEVKELRER
wheat (SIN 20)        ----------------------------------------------------------R
gi_3915029            QVKHSLPPQKREIFDSLQPWAKENLLNLLKPVEKSWQPQDFLPDPSSDGFYDEVKELRER
prickly poppy (SIN 16) QVTHSMPPQKIEIFKSLEDWADSNILIHLKPVEKCWQPQDFLPDASDGFYDQVKELRER
gi_575942             QVTHSMPPQKIEIFKALEDWADNNILVHLKPVEKCWQPQDFLPDPSSDGFDDQVKELRER
prickly poppy (SIN 18) ------------------------------------------------------------
gi_3915030            QVTHSMPPEKREIFDSLHGWADNNILGHLKPVEKCWQASDFLPDPASEGFEDQVKELRER corn (SIN 14)         ANEIPDEYFVCLVGDMVTEEALPTYQTMLNTLDGVRDETGASPTTWAVWTRAWTAEENRH
rice (SIN 20)         AKEIPDDYFVCLVGDMVTEEALPTYQTMLNTLDGVRDETGASPTTWAVWTRAWTAEENRH
wheat (SIN 20)        ANEIPDEYFVCLVGDMVTEEALPTYQTMLNTLDGVRDETGASPTTWAVWTRAWTAEENRH
gi_3915029            AKEIPDDYFVCLVGDMVTEEALPTYQTMLNTLDGVRDETGASPTTWAVWTRAWTAEENRH
prickly poppy (SIN 16) AKEIPDEYFVVLVGDMITEEALPTYQTMLNTLDGVRDETGASPTSWAVWTRAWTAEENRH
gi_575942             AKEIPDDYFVVLVGDMITEEALPTYQTMLNTLDGVRDETGASPTSWAVWTRAWTAEENRH
prickly poppy (SIN 18) -------ICFS--------------LSALS------------------------------
gi_3915030            CKEIPDDYFVVLVGDMITEEALPTYQTMLNTLDGVRDETGASLTPWAIWTRAWTAEENRH
```

FIG. 1A

STEAROYL-ACP DESATURASE ALIGNMENT

```
corn (SIN 14)         GDLLNKYMYLTGRVDMKQIEKTIQYLIGSGMDPGTENNPYLGFLYTSFQERATFVSHGNT
rice (SIN 20)         GDLLNKYMYLTGRVDMKQIEKTIQYLIGSGMDPGTENNPYLGFLYTSFQERATFISHGNT
wheat (SIN 20)        GDLLNKYMYLTGRVDMKQIEKTIQYLIGSGMDPGTENNPYLGFLYTSFQERATFVSHGNT
gi_3915029            GDLLNKYMYLTGRVDMKQIEKTIQYLIGSGMDPGTENNPYLGFLYTSFQERATFISHGNT
prickly poppy (SIN 16) GDLLNKYLYLSGRVDMKQIEKTIQYLIGSGMDPRTENNPYLGFIYTSFQERATFISHGNT
gi_575942             GDLLNKYLYLSGRVDMRQIEKTIQYLIGSGMDPRTEMSPYLGFIYTSFQERATFISHGNT
prickly poppy (SIN 18) ------LSLSLQYLIGSGMDPRMENNPYLGFIYTSFQERATFISHGNT
gi_3915030            GDJLNKYLYLSGRVDMRQIEKTIQYLIGSGMDPRTENNPHLGFIYTSFQERATFISHGNT corn (SIN 14)         ARHAKEYGDLKLAQICGTIAADEKRHETAYTKIVEKLFEMDPDYTVLAFADMMRKKITMP
rice (SIN 20)         ARHAKEYGDLKLAQICGTIAADEKRHETAYTKIVEKLFEIDPDYTVLAFADMMRKKISMP
wheat (SIN 20)        ARHAKEYGDLKLAQICGTLAADEKRHETAYTKIVEKLFEMDPDYTVLAFADMMRKKITMP
gi_3915029            ARHAKEYGDLKLAQICGTIAADEKRHETAYTKIVEKLFEIDPDYTVLAFADMMRNKISMT
prickly poppy (SIN 16) ARHAKEHGDLKLAQICGTIAADEKRHETAYTKISEKLFEIDPDGTILAFADMMRKKIAMP
gi_575942             ARLAREHGDLKLAQICGTIAADEKRHETAYTKIVEKLFEIDPNDTVLAFADMMRKKISMP
prickly poppy (SIN 18) ARHAKEHGDLKLAQICGTIAADEKRHETAYSKIIEKLFEIDPDGTILAFADMMRKKIAMP
gi_3915030            ARHAKEHGDMKLAQVCGIIAADEKRHETAYTKIVEKLFEVDPDGTVLAVADMMRKKISMP corn (SIN 14)         AHLMYDGKDDNLFEHFSAVAQRLGVYTAKDYADILEFLVQRWKVAELTGLSGEGRSAQDF
rice (SIN 20)         AHLMYDGKDDNLFEHFSAVAQRLGVYTAKDYADILEFLVQRWKVADLTGLSGEGRRAQDF
wheat (SIN 20)        AHLMYDGKDDNLFEHFGAVAQRLGVYTAKDYAD---------------------------
gi_3915029            AHLMYDGKDDNLFEHLSAVAQRLGVYTVRDYADMLEFLVQRWKVADLTGLSGEGRRAQDF
prickly poppy (SIN 16) AHLMYDGKDDNLFEHFSSVAQRLGVYTAKDYADILEFLVARWNVEKITGLSGEGRKAQDY
gi_575942             AHLMYDGRDDNLFDHFSSVAQRLGVYTAKDYADILEHLVARWKVANLTGLSADGRKAQDY
prickly poppy (SIN 18) AHLMYDGRDDNLFEHFSAVAQRLGVYTAKDYADILEFLVGRWDVEKITGLSGEGRKAQDY
gi_3915030            AHLMYDGRDDNLFEHFSTVAQRLGVYTAKDYADILEFLVGRWEIEKLTGLSGEGHKARDY
```

FIG. 1B

STEAROYL-ACP DESATURASE ALIGNMENT

```
corn (SIN 14)              VCTLAPRIRRLDDRAQA---RAKQAPVIPFSWVYDRKVQL
rice (SIN 20)              VCTLAPRIRRLDERAQA---RAKQAPVIPFSWVYDRKVQL
wheat (SIN 20)             ----------------------------------------
gi_3915029                 VCTLAPRIRRLDERAQA---RAKQAPVIPFSWVYDRKVQL
prickly poppy (SIN 16)     VCGLTPRIRRLEERAQAQAKKNKQDRHVPFSWIFNKEVLL
gi_575942                  VCGLPPRIRRLEERAQG---RAKQAPKIPFSWIHDREVQL
prickly poppy (SIN 18)     VCGLTPRIRRLEDRAQAQAKKNKQDRQVPFSWLFNKEVLL
gi_3915030                 VCGLAPRIRKLBERAQA---RAKQKAPVPFSWVFGKDIKL
```

FIG. 1C

STEAROYL-CoA DESATURASE ALIGNMENT

```
marigold (SIN 32)  MS----------------------------------------------------------
marigold (SIN 34)  MS------PANYDKSPVTN--NQIRRTNGG-------------------PGY---------
tobacco  (SIN 24)  MALFAPLPSKFKPYPFSPLPQPIHRPARSFFPAQPTKNVTTKTSLLNKWNGYRLEGKVKI
gi_2970034         MSL--------------------------------------------------------- marigold (SIN 32)  ----------------SDGSKELKHRRIIFSDVEVIRKRNLFRGRKWRSLDIKMASGILFF
marigold (SIN 34)  ----------SPDDDQKTQLSSELEKRRKGGFWLRRWSLADVATLCWIVEI
tobacco  (SIN 24)  NRRVMPIVNVASSPVSENGKKSNFNRILFSDVLVKRPRDVLFGRQWNSVDVGSAAVVVGM
gi_2970034         -------SASEKEBNNKKMAADKAEMGRKKRAMWERKWKRLDIVKAFASLFV marigold (SIN 32)  HVLALFAPFTFTWDAFLLAFLCYFLIGILGITMCYHRLLAHRSLKLPKWLEYTCAYLGVQ
marigold (SIN 34)  HMLAACAPFVFDWGAFTVAMGLALLTG-MGMTLGYHRLLTHRSFKIPKMLEYFFAYSGVL
tobacco  (SIN 24)  HLLSLLAPFTENWAAVGIAFGLYIITGLLGITLSFHRNLSHRSFKLPKWLEYLFAYCGVQ
gi_2970034         HFLCLLAPFNFTWPALRVALIVYTVGG-LGITVSYHRNLAHRSFKVPKWLEYFFAYCGLL marigold (SIN 32)  AIQRDPIYWVSIHRYHQYVESENDPHTPTFGEFWFSHMGWLFDSGFIMEKYQER-RNVED
marigold (SIN 34)  AGQKDPISWVSTHKSHHKYSDTDRDPHSPTEGFWFSHIGWFCYSDYIAAKCGGEYSNVPE
tobacco  (SIN 24)  ALQGNPIDWVSTHRYHHQFCDSDKDPHSPIEGFWFSHMSWMFDTDTIVERTGKP-NNVGD
gi_2970034         AIQGDPIDWVSTHRYHHQFTDSDRDPHSPNEGFWFSHLLWLFDTGYLVEKCGRR-TNVED marigold (SIN 32)  LKSQAFYMFIKRTYLMHIFGFGVLVYAWGGFPYLVHIVGVRNVWGLQVTFIVNSACHIWG
marigold (SIN 34)  LKAQWFYREFLHDTYFCHPITLAIILYLYGDFPYLAWGLGIRATLVCHITFVVRSVGHIMG
tobacco  (SIN 24)  LEKQPFYQFIRDTYVFHPVALAAALLYAMGGFPYIVWGMGVRIVWVYHITWLIVNSACHVWG
gi_2970034         LKRQWYYKFLQRTVLYHLLTFGFLLYFGGLSFLTWGMGIGVAMEHHVTCLINSLCHVWG
```

FIG. 2A

STEAROYL-CoA DESATURASE ALIGNMENT

```
marigold (SIN 32)   KRAWNTDDLSRNNWWVALVTFGEGWHNNHHAFEYSARHGLEWWQIDLCWYMIRFLQSIGL
marigold (SIN 34)   DRSWNTIDTSTNNWWTGAISLGEGWHNNHHAFPNSARHGLEWWQVDLTWELIKFLELVGL
tobacco  (SIN 24)   KQAWNTGDLSRNNWWVALLAFGEGWHNNHHAFEYSARHGLEWWQLDMTWYVVRFLQAIGL
gi_2970034          SRTWKTNDTSRNVWWLSVFSFGESWHNNHHAFESSARQGLEWWQIDISWYIVRFLEIIGL marigold (SIN 32)   ATNVKLPTQDHKLKKSFGSNSKFR
marigold (SIN 34)   ATDVKLPTEAEIRRIASLGSKS--
tobacco  (SIN 24)   ATDVRLPTDTHKQRLALADS----
gi_2970034          ATDVKLPSESQRRRMAMV------R
```

PLANT STEAROYL DESATURASES

This application claims priority benefit of U.S. Provisional Application No. 60/110,785 filed Dec. 3, 1998, now pending.

FIELD OF THE INVENTION

This invention is in the field of plant molecular biology. More specifically, this invention pertains to nucleic acid fragments encoding stearoyl desaturases in plants and seeds.

BACKGROUND OF THE INVENTION

Stearoyl-acyl carrier protein (stearoyl-ACP) desaturase, also known as delta-9 desaturase (EC 1.14.99.6), catalyzes the first step in C-18 fatty acid desaturation in plants. This reaction converts stearic acid to oleic acid (stearoyl-ACP to oleoyl-ACP) by introducing a double bond at the 9/10 position of the C18 chain. cDNAs encoding stearoyl-ACP desaturase have been isolated from several plants including safflower, castor, rapeseed, canola, rice and soybean. Different isozymes may be useful for changing the sturated fatty acid content in seed oil.

The oil of prickly poppy is rich in 9-oxooctacosanoate, a delta-9 keto fatty acid. A prickly poppy gene with similarity to stearoyl-ACP desaturase may encode an enzyme which inserts a keto group rather than a double bond at positon 9, or may provide the substrate for further chemistry to make the keto group. Overexpression of this gene in soybeans, corn, etc. may yield oils rich in keto fatty acids which are useful for industrial applications such as drying agents and monomer precursors.

Stearoyl-CoA desaturase (EC 1.14.99.5) is an integral endoplasmic reticulum membrane protein which introduces a second cis bond at the 12 positon of fatty acids bound to membrane glycerolipids. In rose petals a steroyl-CoA desaturase is induced during senesence. Overexpression of a cytoplasmic acyl-CoA desaturase in seeds may be useful to reduce the levels of saturated CoAs reducing the saturated oils in soybeans and corn.

Overexpression of these desaturases in plants may help increase the cold tolerance since the phase transition temperature of lipids in the cellular membranes depends on the degreee of unsaturation of fatty acids of the membrane lipids.

SUMMARY OF THE INVENTION

The present invention relates to isolated polynucleotides comprising a nucleotide sequence encoding a corn stearoyl-ACP desaturase polypeptide of SEQ ID NO:2 and 14, a rice stearoyl-ACP desaturase polypeptide of SEQ ID NO:8 and 20, and a wheat stearoyl-ACP desaturase polypeptide of SEQ ID NO:10 and 22. Additionally, the present invention relates to isolated polynucleotides comprising a nucleotide sequence encoding a first polypeptide of at least 224 amino acids that has at least 86% identity based on the Clustal method of alignment when compared to a polypeptide selected from the group consisting of a prickly poppy stearoyl-ACP desaturase polypeptide of SEQ ID NOs:4, 6, 16, and 18. The present invention also relates to isolated polynucleotides comprising a nucleotide sequence encoding a first polypeptide of at least 60 amino acids that has at least 60% identity based on the Clustal method of alignment when compared to a polypeptide selected from the group consisting of a tobacco stearoyl-CoA desaturase polypeptide of SEQ ID NOs:12 and 24, and a pot marigold stearoyl-CoA desaturase polypeptide of SEQ ID NO:32 and 34. Further, the present invention relates to isolated polynucleotides comprising a nucleotide sequence encoding a first polypeptide of at least 40 amino acids that has at least 60% identity based on the Clustal method of alignment when compared to a polypeptide selected from the group consisting of an *Arabidopsis thaliana* stearoyl-CoA desaturase polypeptide of SEQ ID NOs:22 and 28, a Peruvian lilly stearoyl-CoA desaturase polypeptide of SEQ ID NO:30, a rice stearoyl-CoA desaturase polypeptide of SEQ ID NO:36, a soybean stearoyl-CoA desaturase polypeptide of SEQ ID NO:38, and a grape stearoyl-CoA desaturase polypeptide of SEQ ID NO:40. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, 19, 21, 23, 25, 27, 29, 31, 33, 35, 37, and 39 that codes for the polypeptide selected from the group consisting of SEQ ID NOs:2, 4, 6, 8, 10, 12, 14, 16, 18, 20, 22, 24, 26, 28, 30, 32, 34, 36, 38, and 40. The present invention also relates to an isolated polynucleotide comprising a nucleotide sequences of at least 40 (preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a stearoyl desaturase polypeptide selected from the group consisting of SEQ ID NOs:2, 8, 10, 14, 20, and 22. Also, the present invention relates to a stearoyl desaturase polypeptide of at least 224 amino acids comprising at least 86% homology based on the Clustal method of alignment compared to a polypeptide selected from the group consisting of SEQ ID NOs:4, 6, 16, and 18. Further, the present invention relates to a stearoyl desaturase polypeptide of at least 60 amino acids comprising at least 60% homology based on the Clustal method of alignment compared to a polypeptide selected from the group consisting of SEQ ID NOs:12, 24, 32, and 34. And still further, the present invention relates to a stearoyl desaturase polypeptide of at least 40 amino acids comprising at least 60% homology based on the Clustal method of alignment compared to a polypeptide selected from the group consisting of SEQ ID NOs:22, 28, 30, 36, 38, and 40.

The present invention relates to a method of selecting an isolated polynucleotide that affects the level of expression of a stearoyl desaturase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a stearoyl desaturase polypeptide in the host cell containing the isolated polynucleotide; and comparing the level of a stearoyl desaturase polypeptide in the host cell containing the isolated polynucleotide with the level of a stearoyl desaturase polypeptide in a host cell that does not contain the isolated polynucleotide.

The present invention relates to a method of obtaining a nucleic acid fragment encoding a substantial portion of a stearoyl desaturase polypeptide gene, preferably a plant stearoyl desaturase polypeptide gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39 and the complement of such nucleotide sequences; and amplifying a nucleic acid fragment (preferably a cDNA inserted in a cloning vector) using the oligonucleotide primer. The amplified nucleic acid fragment preferably will encode a portion of a stearoyl desaturase amino acid sequence.

The present invention also relates to a method of obtaining a nucleic acid fragment encoding all or a substantial portion of the amino acid sequence encoding a stearoyl desaturase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a stearoyl desaturase, the method comprising the steps of: (a) transforming a host cell with a chimeric gene comprising a nucleic acid fragment encoding a stearoyl desaturase, operably linked to suitable regulatory sequences; (b) growing the transformed host cell under conditions that are suitable for expression of the chimeric gene wherein expression of the chimeric gene results in production of stearoyl desaturase in the transformed host cell; (c) optionally purifying the stearoyl desaturase expressed by the transformed host cell; (d) treating the stearoyl desaturase with a compound to be tested; and (e) comparing the activity of the stearoyl desaturase that has been treated with a test compound to the activity of an untreated stearoyl desaturase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 shows a comparison of the amino acid sequences of the stearoyl-ACP desaturase from corn (SEQ ID NO:14), rice (SEQ ID NO:20), wheat (SEQ ID NO:22), and prickly poppy (SEQ ID NO:16 and 18) to the stearoyl-ACP desaturases from rice (NCBI Accession No. gi 3915029, SEQ ID NO:41), sesame (NCBI Accession No. gi 575942, SEQ ID NO:42), and wild potato (NCBI Accession No. gi 3915030, SEQ ID NO:43).

FIG. 2 shows a comparison of the amino acid sequences of the stearoyl-CoA desaturase from tobacco (SEQ ID NO:24), and pot marigold (SEQ ID NOs:32 and 34) to the stearoyl-CoA desaturases from Arabidopsis thaliana (NCBI Accession No. gi 2970034, SEQ ID NO:44).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Stearoyl Desaturases

| | | SEQ ID NO | |
|---|---|---|---|
| | Clone Designation | (Nucleotide) | (Amino Acid) |
| Stearoyl-ACP Desaturase | | | |
| Corn [Zea mays] | Contig of: ccase-b.pk0009.g5 cen1.pk0114.a3 cpm1c.pk001.c23 | 1 | 2 |
| Prickly Poppy [Argemone mexicana] | Contig of: pps1c.pk001.a7 pps1c.pk001.n2 pps1c.pk004.o18 | 3 | 4 |
| Prickly Poppy | pps1c.pk001.c15 | 5 | 6 |
| Rice [Oryza sativa] | rls48.pk0012.a5 | 7 | 8 |
| wheat [Triticum aestivum] | wl1n.pk0115.f10 | 9 | 10 |
| Corn | ccase-b.pk0009.g5:fis | 13 | 14 |
| Prickly Poppy | pps1c.pk001.a7:fis | 15 | 16 |
| Prickly Poppy | pps1c.pk001.c15:fis | 17 | 18 |
| Rice | rls48.pk0012.a5:fis | 19 | 20 |
| Wheat | wl1n.pk0115.f10:fis | 21 | 22 |
| Stearoyl-CoA Desaturase | | | |
| Tobacco [Nicotiana benthamiana] | tds1c.pk001.m19 | 11 | 12 |
| Tobacco | tds1c.pk001.m19:fis | 23 | 24 |
| Arabidopsis thaliana | acs2c.pk011.119 | 25 | 26 |
| Arabidopsis thaliana | adf1c.pk003.h6 | 27 | 28 |
| Peruvian Lilly [Alstroemeria caryophylla] | Contig of: eae1c.pk003.a8 eae1c.pk006.k18 | 29 | 30 |
| Pot marigold [Calendula officinalis] | ecs1c.pk003.h21 | 31 | 32 |
| Pot Marigold | ecs1c.pk004.f4 | 33 | 34 |
| Rice | rsl1n.pk008.b9 | 35 | 36 |
| Soybean [Glycine max] | Contig of: sdp4c.pk004.m23 sdp4c.pk004.m24 | 37 | 38 |
| Grape [Vitis sp.] | vlb1c.pk008.c1 | 39 | 40 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 60 contiguous nucleotides, preferably at least 40 contiguous nucleotides, most preferably at least 30 contiguous nucleotides derived from the nucleic acid sequence of the SEQ ID NOs:1, 3, 5, 7, 9, 11, 13, 15, 17, 19, 21, 23, 25, 27, 29, 31, 33, 35, 37, 39, or the complement of such sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39 and the complement of such nucleotide sequences may be used in methods of selecting an isolated polynucleotide that affects the expression of a polypeptide in a plant cell. A method of selecting an isolated polynucleotide that affects the level of expression of a polypeptide in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without ]the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) Biochemistry of Plants 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) Mol. Biotechnol. 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) Plant Cell 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277) and particle-accelerated or "gene gun" transformation technology (Klein et al. (1987) Nature (London) 327:70–73; U.S. Pat. No. 4,945,050, incorporated herein by reference).

Standard recombinant DNA and molecular cloning techniques used herein are well known in the art and are described more fully in Sambrook et al. Molecular Cloning: A Laboratory Manual; Cold Spring Harbor Laboratory Press: Cold Spring Harbor, 1989 (hereinafter "Maniatis").

Nucleic acid fragments encoding at least a portion of several stearoyl desaturases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other stearoyl desaturase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as stearoyl desaturase) preferably a substantial portion of a plant polypeptide of a gene, comprising the steps of: synthesizing an oligonucleotide primer comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, 29, 31, 33, 35, 37, 39, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of fatty acid composition in those cells. Overexpression of any these desaturases in seeds may produce lower levels of saturated oils. Overexpression of the prickly poppy enzyme in corn or soybean may produce oils rich keto fatty acids which are useful for industrial applications.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632)

added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded stearoyl desaturases. An example of a vector for high level expression of the instant polypeptides in a bacterial host is provided (Example 7).

Additionally, the instant polypeptides can be used as a targets to facilitate design and/or identification of inhibitors of those enzymes that may be useful as herbicides. This is desirable because the polypeptides described herein catalyze various steps in lipid desaturation. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn and soybean tissues were prepared. The characteristics of the libraries are described below.

TABLE 2 cDNA Libraries from Corn and Soybean

| Library | Tissue | Clone |
|---|---|---|
| ccase-b | Corn Callus Type II Tissue, Somatic Embryo Formed, Highly Transformable | ccase-b.pk0009.g5 |
| cen1 | Corn Endosperm 10 to 11 Days After Pollination | cen1.pk0114.a3 |
| cpm1c | Corn BMS Treated With 62 Different Chemicals, Then Pooled** | cpm1c.pk001.c23 |
| pps1c | Prickly Poppy Developing Seeds | pps1c.pk001.a7 |
| | | pps1c.pk001.c15 |
| | | pps1c.pk001.n2 |
| | | pps1c.pk004.o18 |
| rls48 | Rice Leaf 15 Days After Germination, 48 Hours After Infection of Strain *Magaporthe grisea* 4360-R-62 (AVR2-YAMO); Resistant | rls48.pk0012.a5 |
| tds1c | *Nicotiana Bentamiana* Seedling | tds1c.pk001.m19 |
| wl1n | Wheat Leaf From 7 Day Old Seedling* | wl1n.pk0115.f10 |
| acs2c | *Arabidopsis Landsberg* erecta fertilized carpels with developing seeds 6–7 days after fertilization. | acs2c.pk011.119 |
| adf1c | *Arabidopsis Landsberg* erecta young flowers before anthesis including shoot apical meristems | adf1c.pk003.h6 |
| eae1c | *Alstroemeria cayophylla* emerging leaf from mature stem | eae1c.pk003.a8 |
| | | eae1c.pk006.k18 |
| ecs1c | Pot marigold (*Calendula officinalis*) developing seeds | ecs1c.pk003.h21 |
| | | ecs1c.pk004.f4 |
| rsl1n | Rice (*Oryza sativa*, YM) 15 day old seedling normalized* | rsl1n.pk008.b9 |
| sdp4c | Soybean (*Glycine max* L.) developing pods 10–12 mm | sdp4c.pk004.m23 |
| vlb1c | Grape (*Vitis* sp.) late stage berries | vlb1c.pk008.c1 |

*These libraries were normalized essentially as described in U. S. Pat. No. 5,482,845, incorporated herein by reference.
**Chemicals used were: chloramphenicol; cyclohexamide; sorbitol; ergosterol; (±) taxifolin; caffeine; trigonelline; diphenyleneiodonium Cl; methotrexate; BHQ; cyclopiazonic acid; nifedipine; verapamil; fluphenazine-N-2-chloroethane; neomycin sulfate; LY 294002; suramin; aurintricarboxylic acid; wortmannin; MAS 7; dipyridamole; zaprinast; 8-bromo-cGMP; A23187; calmidazolium chloride; compound 48/80 trihydrochloride; 1,2-Didecanoyl-rac-glycerol; staurosporine; trequinsin, HCl; FTS; hydroxyurea; aphidicolin; tunicamycin; brefeldin A; Valinomycin; D-Mannose; Hydrogen peroxide; D-galactose; bafilomycin Al; Oligomycin; Ionomycin; paraquat; glutathione; N-acetyl-L-cysteine; nitrilotriacetic acid; mercaptobenzothiazole; diethyldithiocarbarnate; aminotriazole; alpha-amino adipic acid; ancymidol; HC-toxin; okadaic acid; K-252a; A3, hydrochloride; H-7; olomoucine; rapamycin, cyclosporin A; calyculin A; cypermethrin; actinomycin D; cytochalasin B; all are commercially available from various vendors including Calbiochem-Novabiochem Corp. and Sigma Chemical Corp.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding stearoyl desaturases were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Stearoyl-ACP Desaturase

The BLASTX search using the EST sequences from clones listed in Table 3 revealed similarity of the polypeptides encoded by the cDNAs to stearoyl-ACP desaturase from *Oryza sativa* (NCBI Accession No. gi 976257), *Sesamum indicum* (NCBI Accession No. gi 1020096), *Carthamus tinctorius* (NCBI Accession No. gi 134944), *Oryza sativa* (NCBI Accession No. gi 3915029), *Sesamum indicum* (NCBI Accession No. gi 575942), and *Solanum commersonii* (NCBI Accession No. gi 3915030). Shown in Table 3 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 3

BLAST Results for Sequences Encoding Polypeptides Homologous to Stearoyl-ACP Desaturase

| Clone | Status | Accession No. | BLAST pLog Score |
|---|---|---|---|
| Contig of: ccase-b.pk0009.g5 cen1.pk0114.a3 cpm1c.pk001.c23 | Contig | 976257 | 81.22 |
| Contig of: pps1c.pk001.a7 pps1c.pk001.n2 pps1c.pk004.o18 | Contig | 1020096 | 65.40 |
| pps1c.pk001.c15 | EST | 134944 | 66.40 |
| rls48.pk0012.a5 | EST | 976257 | 91.70 |
| wl1n.pk0115.f10 | EST | 976257 | 90.70 |
| ccase-b.pk0009.g5:fis | FIS | 3915029 | 254.00 |
| pps1c.pk001.a7:fis | FIS | 575942 | 254.00 |
| pps1c.pk001.c15:fis | FIS | 3915030 | 254.00 |
| rls48.pk0012.a5:fis | FIS | 3915029 | 254.00 |
| wl1n.pk0115.f10:fis | FIS | 3915029 | 120.00 |

FIG. 1 presents an alignment of the amino acid sequences set forth in SEQ ID NOs:14, 16, 18, 20, and 22, and the *Oryza sativa* (NCBI Accession No. gi 3915029), *Sesamum indicum* (NCBI Accession No. gi 575942), and *Solanum commersonii* (NCBI Accession No. gi 3915030). The data in Table 4 represents a calculation of the percent identity of the amino acid sequences set forth in SEQ ID NOs:14, 16, 18, 20, and 22, and the *Oryza sativa* (NCBI Accession No. gi 3915029), *Sesamum indicum* (NCBI Accession No. gi 575942), and *Solanum commersonii* (NCBI Accession No. gi 3915030) sequences (SEQ ID NOs:42, 43, and 44, respectively).

TABLE 4

Percent Identity of Amino Acid Sequences Deduced From the Nucleotide Sequences of cDNA Clones Encoding Polypeptides Homologous to Stearoyl-ACP Desaturase

| SEQ ID NO. | Percent Identity to 3915029 |
|---|---|
| 14 | 88.2% |
| 20 | 97.9% |
| 22 | 94.9% |

| SEQ ID NO. | Percent Identity to 575942 |
|---|---|
| 16 | 85.1% |

| SEQ ID NO. | Percent Identity to 3915030 |
|---|---|
| 18 | 72.3% |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a stearoyl-ACP desaturase. These sequences represent the first corn, wheat, and prickly poppy sequences encoding stearoyl-ACP desaturase.

Example 4

Characterization of cDNA Clones Encoding Stearoyl-CoA Desaturase

The BLASTX search using the EST sequences from clones listed in Table 5 revealed similarity of the polypeptides encoded by the cDNAs to stearoyl CoA desaturase from *Arabidopsis thaliana* (NCBI Accession No. gi 2970034). Shown in Table 5 are the BLAST results for individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 5

BLAST Results for Sequences Encoding Polypeptides Homologous to Stearoyl-CoA Desaturase

| Clone | Status | BLAST pLog Score 2970034 |
|---|---|---|
| tds1c.pk001.m19 | EST | 26.00 |
| tds1c.pk001.m19:fis | FIS | 106.00 |
| acs2c.pk011.l19 | EST | 42.70 |
| adf1c.pk003.h6 | EST | 6.10 |
| Contig of: | | |
| eae1c.pk003.a8 | Contig | 15.00 |
| eae1c.pk006.k18 | | |
| ecs1c.pk003.h21 | FIS | 99.00 |
| ecs1c.pk004.f4 | FIS | 94.00 |
| rsl1n.pk008.b9 | EST | 21.30 |
| Contig of: | | |
| sdp4c.pk004.m23 | Contig | 9.30 |
| sdp4c.pk004.m24 | | |
| vlb1c.pk008.c1 | EST | 24.05 |

FIG. 2 presents an alignment of the amino acid sequences set forth in SEQ ID NOs:24, 32 and 34, and the *Arabidopsis thaliana* (NCBI Accession No. gi 2970034) sequence (SEQ ID NO:44). The data in Table 6 represents a calculation of the percent identity of the amino acid sequences set forth in SEQ ID NOs:24, 32 and 34, and the *Arabidopsis thaliana* (NCBI Accession No. gi 2970034) sequence (SEQ ID NO:44).

TABLE 6

Percent Identity of Amino Acid Sequences Deduced From the Nucleotide Sequences of cDNA Clones Encoding Polypeptides Homologous to Stearoyl-CoA Desaturase

| SEQ ID NO. | Percent Identity to 2970034 |
|---|---|
| 24 | 51.5% |
| 32 | 52.1% |
| 34 | 42.7% |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a stearoyl CoA desaturase. These sequences represent the first monocot (rice), and the first tobacco, Peruvian lilly, and pot marigold sequences encoding stearoyl CoA desaturase.

Example 5

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of 30 $\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of issue to N6 medium supplemented with 0.2 mg per liter of 2,4-D. After two weeks the issue can be transferred to regeneration medium (Fromm et al. (1990) *Bio/Technology* 8:833–839).

Example 6

Expression of Chimeric Genes in Dicot Cells

A seed-specific expression cassette composed of the promoter and transcription terminator from the gene encoding the $\beta$ subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a himeric gene composed of the 35S promoter from Cauliflower Mosaic Virus (Odell et al. 1985) *Nature* 313:810–812), the hygromycin phosphotransferase gene from plasmid pJR225 from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 $\mu$L of a 60 mg/mL 1 $\mu$m gold particle suspension is added (in order): 5 $\mu$L DNA (1 $\mu$g/$\mu$L), 20 $\mu$l spermidine (0.1 M), and 50 $\mu$L CaCl$_2$ (2.5 M). The particle preparation is then agitated for three minutes, spun in a microfuge for 10 seconds and the supernatant removed. The DNA-coated particles are then washed once in 400 $\mu$L 70% ethanol and resuspended in 40 $\mu$L of anhydrous ethanol. The DNA/particle suspension can be sonicated three times for one second each. Five $\mu$L of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 7

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 8

Evaluating Compounds for Their Ability to Inhibit the Activity of Stearoyl Desaturases The polypeptides described herein may be produced using any number of methods known to those skilled in the art. Such methods include, but are not limited to, expression in bacteria as described in Example 7, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a $(His)_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for stearoyl-ACP desaturases are presented by Merlo, A. O. et al. (1998) *Plant J.* 10:1603–1621. Assays for stearoyl-CoA desaturase are presented by Diczfalusy U., et al. (1995) *Biochim Biophys Acta* 1259:313–316.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a nucleotide sequence encoding a polypeptide having stearoyl-ACP desaturase activity, wherein the amino acid sequence of the polypeptide and the amino acid sequence of SEQ D NO:14 have a sequence identity of at least 90% based on the Clustal method of alignment; or
   (b) the complement of the nucleotide sequence, of (a) wherein the complement and the nucleotide sequence contain the same number of nucleotides and are 100% complementary.

2. The polynucleotide of claim 1 wherein the amino acid sequence of the polypeptide and the amino acid sequence of SEQ ID NO:14 have at least 95% sequence identity based on the Clustal alignment method.

3. The polynucleotide of claim 1, wherein the amino acid sequence of the polypeptide comprises the amino acid sequence of SEQ ID NO:14.

4. The polynucleotide of claim 1, wherein the nucleotide sequence comprises the nucleotide sequence of SEQ ID NO:13.

5. A chimeric gene comprising the polynucleotide of claim 1 operably linked to at least one regulatory sequence.

6. A cell comprising the polynucleotide of claim 1.

7. The cell of claim 6, wherein the cell is selected from the group consisting of a yeast cell, a bacterial cell and a plant cell.

8. A virus comprising the polynucleotide of claim 1.

9. A transgenic plant comprising the polynucleotide of claim 1.

10. A method for transforming a cell comprising introducing into a cell the polynucleotide of claim 1.

11. A method for producing a transgenic plant comprising (a) transforming a plant cell with the polynucleotide of claim 1 and (b) regenerating a plant from the transformed plant cell.

12. A vector comprising the polynucleotide of claim 1.

13. A plant comprising the chimeric gene of claim 5.

14. A seed comprising the chimeric gene of claim 5.

15. A method for isolating a polypeptide encoded by the polynucleotide of claim 1 comprising isolating the polypeptide from a cell containing a recombinant DNA construct comprising the polynucleotide operably linked to a regulatory sequence.

* * * * *

UNITED STATES PATENT AND TRADEMARK OFFICE
CERTIFICATE OF CORRECTION

| | | |
|---|---|---|
| PATENT NO. | : 6,762,345 B1 | |
| DATED | : July 13, 2004 | |
| INVENTOR(S) | : Cahoon, Rebecca E., Famodu, Omolayo O. and Shen, Jennie B. | |

It is certified that error appears in the above-identified patent and that said Letters Patent is hereby corrected as shown below:

<u>Title page,</u>
Item [56], References Cited, OTHER PUBLICATIONS, "Cho et al." reference, after "vol." delete "108" and insert therefor -- 107 --.

<u>Column 3,</u>
Line 65, delete "FIG. 1 shows" and insert therefor -- Figures 1A, 1B and 1C show --.

<u>Column 4,</u>
Line 6, delete "FIG. 2 shows" and insert therefor -- Figures 2A and 2B show --.

<u>Column 7,</u>
Lines 38-39, delete "; see also www.ncbi.nlm.nih.gov/BLAST/".
Line 67, before "the" delete "]".

<u>Column 17,</u>
Lines 20-21, delete "; see also www.ncbi.nlm.nih.gov/BLAST/"

<u>Column 18,</u>
Line 22, delete "FIG. 1 presents" and insert therefor -- Figures 1A-1C present --.

<u>Column 19,</u>
Line 40, delete "FIG. 2 presents" and insert therefor -- Figures 2A-2B present --.

<u>Column 81,</u>
Line 22, after "sequence" delete ",". Also after "(a)" insert -- , --.

Signed and Sealed this

Tenth Day of May, 2005

JON W. DUDAS
*Director of the United States Patent and Trademark Office*

SEQUENCE LISTING

<160> NUMBER OF SEQ ID NOS: 44

<210> SEQ ID NO 1
<211> LENGTH: 591
<212> TYPE: DNA
<213> ORGANISM: Zea mays
<220> FEATURE:
<221> NAME/KEY: unsure
<222> LOCATION: (571)
<223> OTHER INFORMATION: n is a, c, g or t

<400> SEQUENCE: 1

```
ggctgcacac acaaggaagg ggacaaccac aagcgcctaa gatcccgtcc tccgcgtcga      60
gatctttgcc gaggcggtga ccgtcgaggg atcgccatgg cgttgagggc gtccccgtg     120 tcgctggcac cgcggcagcg ccgctgccgc ctttcgcgcg gaggaggatg gcccgggtgg    180
tggccatggc gtccaccatc aacagggtca aaactgtcaa agaaccctat acccctccac    240
gagaggtaca tcgccaaatt acccattcac taccacctca aaagcgggag attttcgatt    300
cacttcaacc ttgggccaag gataacctac tgaacctact gaagccagtt gaaaagtcat    360
ggcagccaca ggacttccta ccagagcctt cttctgatgg gttttatgat gaagttaaag    420
aactgaggga gcgggcaaat gaaatacctg atgaatactt tgtttgctta gttggtgata    480
tggttactga ggaagcctta cctacatacc aaacaatgct taacactctt gatggagtcc    540
gggatgaaac tggtgcaagt ccaaacactt nggccggttt ggcaaaggca t             591
```

<210> SEQ ID NO 2
<211> LENGTH: 141
<212> TYPE: PRT
<213> ORGANISM: Zea mays
<220> FEATURE:
<221> NAME/KEY: UNSURE
<222> LOCATION: (135)
<223> OTHER INFORMATION: Xaa can be any naturally occurring amino acid

<400> SEQUENCE: 2

```
Met Ala Arg Val Val Ala Met Ala Ser Thr Ile Asn Arg Val Lys Thr
  1               5                  10                  15

Val Lys Glu Pro Tyr Thr Pro Pro Arg Glu Val His Arg Gln Ile Thr
             20                  25                  30

His Ser Leu Pro Pro Gln Lys Arg Glu Ile Phe Asp Ser Leu Gln Pro
         35                  40                  45

Trp Ala Lys Asp Asn Leu Leu Asn Leu Leu Lys Pro Val Glu Lys Ser
     50                  55                  60

Trp Gln Pro Gln Asp Phe Leu Pro Glu Pro Ser Ser Asp Gly Phe Tyr
 65                  70                  75                  80

Asp Glu Val Lys Glu Leu Arg Glu Arg Ala Asn Glu Ile Pro Asp Glu
                 85                  90                  95
```

```
Tyr Phe Val Cys Leu Val Gly Asp Met Val Thr Glu Glu Ala Leu Pro
            100                 105                 110

Thr Tyr Gln Thr Met Leu Asn Thr Leu Asp Gly Val Arg Asp Glu Thr
        115                 120                 125

Gly Ala Ser Pro Asn Thr Xaa Ala Gly Leu Ala Lys Ala
    130                 135                 140

<210> SEQ ID NO 3
<211> LENGTH: 563
<212> TYPE: DNA
<213> ORGANISM: Argemone mexicana
<220> FEATURE:
<221> NAME/KEY: unsure
<222> LOCATION: (304)
<223> OTHER INFORMATION: n is a, c, g or t
<220> FEATURE:
<221> NAME/KEY: unsure
<222> LOCATION: (520)
<223> OTHER INFORMATION: n is a, c, g or t
<220> FEATURE:
<221> NAME/KEY: unsure
<222> LOCATION: (537)
<223> OTHER INFORMATION: n is a, c, g or t
<220> FEATURE:
<221> NAME/KEY: unsure
<222> LOCATION: (542)
<223> OTHER INFORMATION: n is a, c, g or t

<400> SEQUENCE: 3
ggaaagcaaa atagaaggcg tctagagagg gaaagagaaa aaaagagaga gagagaaaaa        60
aagaagagaa aatggctctg aaactcaatc ccttaacttt tcaatctcaa aagtttccat       120
gttttggttt ccctaatgtt gccaatgtca gatctccaaa ggttttcatg gcttcaaccc       180
ttcgttccaa gctcgtctaa ggagacggag aagctcaaga aaccctttac ccctccacgt       240
gaggtacacg ttcaagtcac ccactctatg ccaccacaga agattgagat cttcaagtcc       300
ttanaggatt gggcaagata gtaacatctt gatacacctt aagcctgttg agaaatgttg       360
gcaaccacaa gactttctac ctgatccaag cctcagatgg gttttatgat caagtcaagg       420
agctaagaga gagagcaaag gaaattccgg atgaatactt tgttgttttg ggttggggat       480
atgatcactg aggaagccct tccaacatat caaacatgcn taacacaatt agatggngtc       540
anggatgaac aagtgcgaat cca                                                563

<210> SEQ ID NO 4
<211> LENGTH: 157
<212> TYPE: PRT
<213> ORGANISM: Argemone mexicana
<220> FEATURE:
<221> NAME/KEY: UNSURE
<222> LOCATION: (77)
<223> OTHER INFORMATION: Xaa can be any naturally occurring amino acid
<220> FEATURE:
<221> NAME/KEY: UNSURE
<222> LOCATION: (148)
<223> OTHER INFORMATION: Xaa can be any naturally occurring amino acid
<220> FEATURE:
<221> NAME/KEY: UNSURE
<222> LOCATION: (155)
<223> OTHER INFORMATION: Xaa can be any naturally occurring amino acid

<400> SEQUENCE: 4

Met Ala Leu Lys Leu Asn Pro Leu Thr Phe Gln Ser Gln Lys Phe Pro
  1               5                  10                  15

Cys Phe Gly Phe Pro Asn Val Ala Asn Val Arg Ser Pro Lys Val Phe
             20                  25                  30
```

```
Met Ala Ser Thr Leu Arg Ser Ser Lys Glu Thr Glu Lys Leu Lys
        35                  40                  45

Lys Pro Phe Thr Pro Pro Arg Glu Val His Val Gln Val Thr His Ser
 50                  55                  60

Met Pro Pro Gln Lys Ile Glu Ile Phe Lys Ser Leu Xaa Asp Trp Ala
 65                  70                  75                  80

Asp Ser Asn Ile Leu Ile His Leu Lys Pro Val Glu Lys Cys Trp Gln
                 85                  90                  95

Pro Gln Asp Phe Leu Pro Asp Pro Ser Ser Asp Gly Phe Tyr Asp Gln
            100                 105                 110

Val Lys Glu Leu Arg Glu Arg Ala Lys Glu Ile Pro Asp Glu Tyr Phe
        115                 120                 125

Val Val Leu Val Gly Asp Met Ile Thr Glu Glu Ala Leu Pro Thr Tyr
130                 135                 140

Gln Thr Cys Xaa Thr Gln Leu Asp Gly Val Xaa Asp Glu
145                 150                 155

<210> SEQ ID NO 5
<211> LENGTH: 418
<212> TYPE: DNA
<213> ORGANISM: Argemone mexicana

<400> SEQUENCE: 5
attccttcct cttctccaaa aaaataaat caaatctgtt tcagtctctc agctctctct      60
ctctctctct ctctccagta tcttattggg tcgggaatgg atcctcgaat ggaaaacaac    120
ccatatctgg gattcatcta cacctcattc caggagaggg caactttcat ctcccacgga    180
aacacggcta gacatgcgaa ggagcatggg gacttaaaac tggctcaaat atgtggaacc    240
attgctgctg atgaaaagcg ccacgaaact gcttattcta agatcatcga aaagcttttt    300
gagattgacc cagatggtac tatcttggcc tttgctgata tgatgaggaa gaaaattgca    360
atgccaagcc cacttaatgt atgacggtag ggatgacaat ctctttgagc acttctca     418

<210> SEQ ID NO 6
<211> LENGTH: 102
<212> TYPE: PRT
<213> ORGANISM: Argemone mexicana

<400> SEQUENCE: 6

Ser Leu Gln Tyr Leu Ile Gly Ser Gly Met Asp Pro Arg Met Glu Asn
 1               5                  10                  15

Asn Pro Tyr Leu Gly Phe Ile Tyr Thr Ser Phe Gln Glu Arg Ala Thr
             20                  25                  30

Phe Ile Ser His Gly Asn Thr Ala Arg His Ala Lys Glu His Gly Asp
         35                  40                  45

Leu Lys Leu Ala Gln Ile Cys Gly Thr Ile Ala Ala Asp Glu Lys Arg
     50                  55                  60

His Glu Thr Ala Tyr Ser Lys Ile Ile Glu Lys Leu Phe Glu Ile Asp
 65                  70                  75                  80

Pro Asp Gly Thr Ile Leu Ala Phe Ala Asp Met Met Arg Lys Lys Ile
             85                  90                  95

Ala Met Pro Ser Pro Leu
            100

<210> SEQ ID NO 7
<211> LENGTH: 604
```

```
<212> TYPE: DNA
<213> ORGANISM: Oryza sativa
<220> FEATURE:
<221> NAME/KEY: unsure
<222> LOCATION: (59)
<223> OTHER INFORMATION: n is a, c, g or t
<220> FEATURE:
<221> NAME/KEY: unsure
<222> LOCATION: (416)
<223> OTHER INFORMATION: n is a, c, g or t
<220> FEATURE:
<221> NAME/KEY: unsure
<222> LOCATION: (423)
<223> OTHER INFORMATION: n is a, c, g or t
<220> FEATURE:
<221> NAME/KEY: unsure
<222> LOCATION: (567)
<223> OTHER INFORMATION: n is a, c, g or t
<220> FEATURE:
<221> NAME/KEY: unsure
<222> LOCATION: (582)
<223> OTHER INFORMATION: n is a, c, g or t
<220> FEATURE:
<221> NAME/KEY: unsure
<222> LOCATION: (584)
<223> OTHER INFORMATION: n is a, c, g or t
<220> FEATURE:
<221> NAME/KEY: unsure
<222> LOCATION: (598)
<223> OTHER INFORMATION: n is a, c, g or t
<220> FEATURE:
<221> NAME/KEY: unsure
<222> LOCATION: (604)
<223> OTHER INFORMATION: n is a, c, g or t

<400> SEQUENCE: 7
tgtatcagca gaagtccagg tggacaagaa cgcgaggagg ggaaagaatc atccccgang      60
atctcgctgc cgctgctcat ggcgttcgcg gcgtcccaca ccgcatcgcc gtcctcctgc     120
ggcggcgtgg cgcagaggag gagcaatggg atgtcgccgg tggtggccat ggcctccacc     180
atcaacaggg tcaagactgc taagaagccc tacactcctc cacgtgaagt tcatctccaa     240
gtcaagcatt cactgccacc ccaaaagcgg gagattttcg attcgcttca accttgggcc     300
aaagagaacc ttttgaacct cctgaagcca gttgagaagt catggcagcc acaggacttc     360
ctgccagacc cttcttccga tgggttttat gatgaagtaa agagctgcg ggaganggct     420 aangagatcc ctgatgacta ctttgtttgc ttagttggag acatggttac tgaggaactc     480
ttcctaccta tcaaaacaat gcttaacacc cttgatggtg tccgagatga aactggcgca     540
agccaaccac tgggctgttt ggacaanaca tggactgctg ananaaaagc atgtgatntt     600 cttn                                                                 604

<210> SEQ ID NO 8
<211> LENGTH: 155
<212> TYPE: PRT
<213> ORGANISM: Oryza sativa
<220> FEATURE:
<221> NAME/KEY: UNSURE
<222> LOCATION: (113)
<223> OTHER INFORMATION: Xaa can be any naturally occurring amino acid
<220> FEATURE:
<221> NAME/KEY: UNSURE
<222> LOCATION: (115)
<223> OTHER INFORMATION: Xaa can be any naturally occurring amino acid

<400> SEQUENCE: 8

Met Ala Phe Ala Ala Ser His Thr Ala Ser Pro Ser Ser Cys Gly Gly
 1               5                  10                  15

Val Ala Gln Arg Arg Ser Asn Gly Met Ser Pro Val Val Ala Met Ala
```

```
                    20                  25                  30
Ser Thr Ile Asn Arg Val Lys Thr Ala Lys Pro Tyr Thr Pro Pro
            35                  40                  45

Arg Glu Val His Leu Gln Val Lys His Ser Leu Pro Pro Gln Lys Arg
    50                  55                  60

Glu Ile Phe Asp Ser Leu Gln Pro Trp Ala Lys Glu Asn Leu Leu Asn
65                  70                  75                  80

Leu Leu Lys Pro Val Glu Lys Ser Trp Gln Pro Gln Asp Phe Leu Pro
                85                  90                  95

Asp Pro Ser Ser Asp Gly Phe Tyr Asp Glu Val Lys Glu Leu Arg Glu
            100                 105                 110

Xaa Ala Xaa Glu Ile Pro Asp Asp Tyr Phe Val Cys Leu Val Gly Asp
        115                 120                 125

Met Val Thr Glu Glu Leu Phe Leu Pro Ile Lys Thr Met Leu Asn Thr
130                 135                 140

Leu Asp Gly Val Arg Asp Glu Thr Gly Ala Ser
145                 150                 155

<210> SEQ ID NO 9
<211> LENGTH: 592
<212> TYPE: DNA
<213> ORGANISM: Triticum aestivum
<220> FEATURE:
<221> NAME/KEY: unsure
<222> LOCATION: (463)
<223> OTHER INFORMATION: n is a, c, g or t
<220> FEATURE:
<221> NAME/KEY: unsure
<222> LOCATION: (495)
<223> OTHER INFORMATION: n is a, c, g or t
<220> FEATURE:
<221> NAME/KEY: unsure
<222> LOCATION: (528)
<223> OTHER INFORMATION: n is a, c, g or t
<220> FEATURE:
<221> NAME/KEY: unsure
<222> LOCATION: (546)
<223> OTHER INFORMATION: n is a, c, g or t
<220> FEATURE:
<221> NAME/KEY: unsure
<222> LOCATION: (558)
<223> OTHER INFORMATION: n is a, c, g or t
<220> FEATURE:
<221> NAME/KEY: unsure
<222> LOCATION: (572)
<223> OTHER INFORMATION: n is a, c, g or t
<220> FEATURE:
<221> NAME/KEY: unsure
<222> LOCATION: (576)
<223> OTHER INFORMATION: n is a, c, g or t
<220> FEATURE:
<221> NAME/KEY: unsure
<222> LOCATION: (588)
<223> OTHER INFORMATION: n is a, c, g or t

<400> SEQUENCE: 9
gcgggcaaat gaaatacctg atgaatactt tgtttgctta gttggtgata tggttactga      60
ggaagcctta cctacatacc aaacaatgct taacactctt gatggagtcc gggatgaaac     120
tggtgcaagt ccaaccacgt gggcggtttg acaagggca tggacagctg aagagaacag      180
acatggtgac ctccttaaca agtacatgta ccttactgga cgggttgaca tgaaacaaat     240
tgagaagacc atacaatatc tgattggttc cggaatggat cctggaactg agaacaaccc     300
ctacttgggt ttcctctaca catcattcca agaaagggca acatttgtgt cgcatgggaa     360
tactgcaagg catgccaagg agtatggtga tctcaagctg gccagatatg tggcacgata     420
```

```
caaccgatga gaaacgccac gaaacaacct acacaagata tcnagaaact cttcgagatg      480
gacctgatta cacantgctg gcgttgctga catgatgagg aagaagtnac atgcagccat      540
ccattncacg taagacanac tgttcaacac tncgcncgtg gccaaagntg gc              592
```

<210> SEQ ID NO 10
<211> LENGTH: 135
<212> TYPE: PRT
<213> ORGANISM: Triticum aestivum

<400> SEQUENCE: 10

```
Arg Ala Asn Glu Ile Pro Asp Glu Tyr Phe Val Cys Leu Val Gly Asp
  1               5                  10                  15

Met Val Thr Glu Glu Ala Leu Pro Thr Tyr Gln Thr Met Leu Asn Thr
             20                  25                  30

Leu Asp Gly Val Arg Asp Glu Thr Gly Ala Ser Pro Thr Thr Trp Ala
         35                  40                  45

Val Trp Thr Arg Ala Trp Thr Ala Glu Glu Asn Arg His Gly Asp Leu
     50                  55                  60

Leu Asn Lys Tyr Met Tyr Leu Thr Gly Arg Val Asp Met Lys Gln Ile
 65                  70                  75                  80

Glu Lys Thr Ile Gln Tyr Leu Ile Gly Ser Gly Met Asp Pro Gly Thr
                 85                  90                  95

Glu Asn Asn Pro Tyr Leu Gly Phe Leu Tyr Thr Ser Phe Gln Glu Arg
            100                 105                 110

Ala Thr Phe Val Ser His Gly Asn Thr Ala Arg His Ala Lys Glu Tyr
        115                 120                 125

Gly Asp Leu Lys Leu Ala Arg
    130                 135
```

<210> SEQ ID NO 11
<211> LENGTH: 520
<212> TYPE: DNA
<213> ORGANISM: Nicotiana benthamiana
<220> FEATURE:
<221> NAME/KEY: unsure
<222> LOCATION: (495)
<223> OTHER INFORMATION: n is a, c, g or t
<220> FEATURE:
<221> NAME/KEY: unsure
<222> LOCATION: (506)
<223> OTHER INFORMATION: n is a, c, g or t
<220> FEATURE:
<221> NAME/KEY: unsure
<222> LOCATION: (514)
<223> OTHER INFORMATION: n is a, c, g or t
<220> FEATURE:
<221> NAME/KEY: unsure
<222> LOCATION: (518)
<223> OTHER INFORMATION: n is a, c, g or t

<400> SEQUENCE: 11

```
ttttttgct agcaaattga ccaaatgtgg tttcattcca agttgttaca aaacaagagc       60
agaagaaaga agcttcaccc gtgtgctcaa tgtatagtct caccttagtt acattagtag     120
gcaacaagtc acccaaaaat ctcattttca tgtgatacac ttggacgaag ttgaaccgat     180
attgtatttt tcctaactgt cagctaaagc cagcctctgt ttatgagtgt cagttggcaa     240
cctgacatca gtggccaatc caatagcttg aagaaacctt actacatacc aagtcatgtc     300
aagttgccac cattctaagc cgtgcctagc cgaatactcg aacgcatggt ggttattgtg     360
ccaaccttct ccaaatgcaa gcaatgccac ccaccagttg ttccttgaaa ggtcaccaag     420
```

```
tattccatgc ctgctttccc caaacgtggc atgctgaatt tacaagccaa gttatgtggg      480
aaacccaaac aaatnccaac cccaangccc aaanaatnta                            520

<210> SEQ ID NO 12
<211> LENGTH: 72
<212> TYPE: PRT
<213> ORGANISM: Nicotiana benthamiana

<400> SEQUENCE: 12

Gly Asp Leu Ser Arg Asn Asn Trp Trp Val Ala Leu Leu Ala Phe Gly
 1               5                  10                  15

Glu Gly Trp His Asn Asn His His Ala Phe Glu Tyr Ser Ala Arg His
            20                  25                  30

Gly Leu Glu Trp Trp Gln Leu Asp Met Thr Trp Tyr Val Val Arg Phe
        35                  40                  45

Leu Gln Ala Ile Gly Leu Ala Thr Asp Val Arg Leu Pro Thr Asp Thr
    50                  55                  60

His Lys Gln Arg Leu Ala Leu Ala
 65                  70

<210> SEQ ID NO 13
<211> LENGTH: 1623
<212> TYPE: DNA
<213> ORGANISM: Zea mays

<400> SEQUENCE: 13
agaggctgca cacacaagga agggacaac cacaagcgcc taagatcccg tcctccgcgt       60
cgagatcttt gccgaggcgg tgaccgtcga gggatcgcca tggcgttgag ggcgtccccc     120
gtgtcgcatg gcaccgcggc agcgccgctg ccgccttttcg cgcggaggag gatggcccgt    180
ggggtggtgg tggccatggc gtccaccatc aacagggtca aaactgtcaa agaaccctat    240 accctccac gagaggtaca tcgccaaatt acccattcac taccacctca aaagcgggag     300
attttcgatt cacttcaacc ttgggccaag ataacctac tgaacctact gaagccagtt     360
gaaaagtcat ggcagccaca ggacttccta ccagagcctt cttctgatgg gttttatgat    420
gaagttaaag aactgaggga gcgggcaaat gaaatacctg atgaatactt tgtttgctta    480
gttggtgata tggttactga ggaagcctta cctacatacc aaacaatgct taacactctt    540
gatggagtcc gggatgaaac tggtgcaagt ccaaccacgt gggcggtttg acaagggca    600 tggacagctg aagagaacag acatggtgac ctccttaaca agtacatgta ccttactgga    660
cgggttgaca tgaaacaaat tgagaagacc atacaatatc tgattggttc cggaatggat    720
cctggaactg agaacaaccc ctacttgggt ttcctctaca catcattcca agaaagggca    780
acatttgtgt cgcatgggaa tactgcaagg catgccaagg agtatggtga tctcaagctg    840
gcccagatat gtggcacgat agcagccgat gagaagcgcc acgaaacagc ctacaccaag    900
atagtcgaga agctcttcga gatggaccct gattacacag tgcttgcgtt tgctgacatg    960
atgaggaaga agatcacgat gccagcccat ctcatgtacg acggtaagga cgacaacctg   1020
ttcgagcact tcagcgcggt ggcgcagagg ctgggcgtct acaccgccaa agactacgcc   1080
gacatcctcg agttcctggt ccagaggtgg aaagtcgcgg agctcacagg gctgtctgga   1140
gaagggagaa gcgcgcagga ctttgtctgt accttggcgc cgaggatcag gcggctggat   1200
gatagagctc aagcgagggc gaagcaagca ccggttattc ctttcagttg ggtttatgac   1260
cgcaaggtgc agctttaatc aagaacgcta ggcaatgtgg gcatttacta cgtatatcat   1320
```

-continued

```
tttcagtcct ggggttctct ataagaaaca gtctctaggt tatctagcag ggtagaattc    1380
aactactcgt ggatctcact cggtgcaaag tagtgcaaag tacgctatct gttgttaccg    1440
tgcaagctgc agagtttgga ttactatgtg ggcctggtgg tggagaggaa ttctgtgggg    1500
tgcctgcagc cagttatgag tggcagctcc atcgcaactg agttgttgta ttgaatatgt    1560
tacaggacct atagtaaccg aaagtaataa tatggagttt gtataaaaaa aaaaaaaaa     1620 aaa                                                                 1623
```

<210> SEQ ID NO 14
<211> LENGTH: 392
<212> TYPE: PRT
<213> ORGANISM: Zea mays

<400> SEQUENCE: 14

```
Met Ala Leu Arg Ala Ser Pro Val Ser His Gly Thr Ala Ala Pro
 1               5                  10                  15

Leu Pro Pro Phe Ala Arg Arg Met Ala Arg Gly Val Val Val Ala
                20                  25                  30

Met Ala Ser Thr Ile Asn Arg Val Lys Thr Val Lys Glu Pro Tyr Thr
                35                  40                  45

Pro Pro Arg Glu Val His Arg Gln Ile Thr His Ser Leu Pro Pro Gln
        50                  55                  60

Lys Arg Glu Ile Phe Asp Ser Leu Gln Pro Trp Ala Lys Asp Asn Leu
 65                  70                  75                  80

Leu Asn Leu Leu Lys Pro Val Glu Lys Ser Trp Gln Pro Gln Asp Phe
                85                  90                  95

Leu Pro Glu Pro Ser Ser Asp Gly Phe Tyr Asp Glu Val Lys Glu Leu
                100                 105                 110

Arg Glu Arg Ala Asn Glu Ile Pro Asp Glu Tyr Phe Val Cys Leu Val
                115                 120                 125

Gly Asp Met Val Thr Glu Glu Ala Leu Pro Thr Tyr Gln Thr Met Leu
    130                 135                 140

Asn Thr Leu Asp Gly Val Arg Asp Glu Thr Gly Ala Ser Pro Thr Thr
145                 150                 155                 160

Trp Ala Val Trp Thr Arg Ala Trp Thr Ala Glu Glu Asn Arg His Gly
                165                 170                 175

Asp Leu Leu Asn Lys Tyr Met Tyr Leu Thr Gly Arg Val Asp Met Lys
                180                 185                 190

Gln Ile Glu Lys Thr Ile Gln Tyr Leu Ile Gly Ser Gly Met Asp Pro
                195                 200                 205

Gly Thr Glu Asn Asn Pro Tyr Leu Gly Phe Leu Tyr Thr Ser Phe Gln
    210                 215                 220

Glu Arg Ala Thr Phe Val Ser His Gly Asn Thr Ala Arg His Ala Lys
225                 230                 235                 240

Glu Tyr Gly Asp Leu Lys Leu Ala Gln Ile Cys Gly Thr Ile Ala Ala
                245                 250                 255

Asp Glu Lys Arg His Glu Thr Ala Tyr Thr Lys Ile Val Glu Lys Leu
                260                 265                 270

Phe Glu Met Asp Pro Asp Tyr Thr Val Leu Ala Phe Ala Asp Met Met
                275                 280                 285

Arg Lys Lys Ile Thr Met Pro Ala His Leu Met Tyr Asp Gly Lys Asp
    290                 295                 300

Asp Asn Leu Phe Glu His Phe Ser Ala Val Ala Gln Arg Leu Gly Val
```

```
                305                 310                 315                 320
Tyr Thr Ala Lys Asp Tyr Ala Asp Ile Leu Glu Phe Leu Val Gln Arg
                325                 330                 335

Trp Lys Val Ala Glu Leu Thr Gly Leu Ser Gly Glu Gly Arg Ser Ala
            340                 345                 350

Gln Asp Phe Val Cys Thr Leu Ala Pro Arg Ile Arg Arg Leu Asp Asp
        355                 360                 365

Arg Ala Gln Ala Arg Ala Lys Gln Ala Pro Val Ile Pro Phe Ser Trp
    370                 375                 380

Val Tyr Asp Arg Lys Val Gln Leu
385                 390

<210> SEQ ID NO 15
<211> LENGTH: 1624
<212> TYPE: DNA
<213> ORGANISM: Argemone mexicana

<400> SEQUENCE: 15
```

| | | | | | |
|---|---|---|---|---|---|
| gcacgagaga | gaaaaaaaga | gagagagaga | aaaaagaag | agaaaatggc | tctgaaactc | 60 |
| aatcccttaa | cttttcaatc | tcaaaagttt | ccatgttttg | gtttccctaa | tgttgccaat | 120 |
| gtcagatctc | caaggtttt | catggcttca | cccttcgtt | ccagctcgtc | taaggagacg | 180 |
| gagaagctca | agaaacccctt | taccccctcca | cgtgaggtac | acgttcaagt | cacccactct | 240 |
| atgccaccac | agaagattga | gatcttcaag | tccttagagg | attgggcaga | tagtaacatc | 300 |
| ttgatacacc | ttaagcctgt | tgagaaatgt | tggcaaccac | aagactttct | acctgatcca | 360 |
| gcctcagatg | ggttttatga | tcaagtcaag | gagctaagag | agagagcaaa | ggaaattccg | 420 |
| gatgaatact | ttgttgtttt | ggttggggat | atgatcactg | aggaagccct | tccaacatat | 480 |
| caaaccatgc | ttaacacatt | agatggagtc | agggatgaaa | caggtgcgag | tccaacttct | 540 |
| tgggctgttt | ggactagggc | gtggactgcc | aagagaata | ggcatgggga | ccttcttaat | 600 |
| aagtacctct | atctatctgg | ccgagtagat | atgaaacaaa | ttgagaagac | aattcagtat | 660 |
| ttaattgggt | ccggaatgga | tcctcgaaca | gaaaacaacc | catatcttgg | attcatctac | 720 |
| acctcattcc | aagagagggc | aactttcatc | tcccacggaa | acacagctag | gcatgcaaag | 780 |
| gagcacggag | acttgaaact | ggcacaaata | tgtggaacca | ttgctgctga | tgaaaagcgc | 840 |
| catgaaactg | cttataccaa | aatctctgaa | agcttttcg | agattgaccc | agatggtact | 900 |
| atcttagctt | ttgcagatat | gatgaggaaa | aaaattgcta | tgccagccca | cttaatgtat | 960 |
| gacggtaaag | atgacaacct | cttcgagcac | ttctcatcag | ttgctcaacg | gcttggagtt | 1020 |
| tacactgcca | agattatgc | cgatatatta | gaatttctcg | tggctaggtg | gaatgtagag | 1080 |
| aaaataacgg | gtttatccgg | agaaggaagg | aaagctcaag | attacgtgtg | tggcttgaca | 1140 |
| ccaaggatca | gaagattgga | agagagagct | caagctcaag | caaagaaaaa | caagcaagat | 1200 |
| cgccatgttc | ctttcagctg | gatttcaat | aaagaagtgt | tgctttaaat | cggtattgta | 1260 |
| aaatcgagat | caggtgcact | ctctttacca | atcttttcag | acattaatgg | aatagaaatg | 1320 |
| gaaattatgt | caaattgcat | tttgagatct | caactttcca | ttttgattct | cttttatgt | 1380 |
| atgaggagat | aaatttagga | gtgtagttgg | attaagggat | ggatttcgga | gatagagact | 1440 |
| catgcttttt | tcttccggt | tttgatctca | tagttatatc | gaatatcaga | cgattagggc | 1500 |
| gaggttagta | tagtttgttt | ttgttttcgt | ttttgttggg | tgtgttttgc | ttgtatgttt | 1560 |
| cttttttta | tttattatat | ttataaatta | agctctcatt | agtaataaaa | aaaaaaaaaa | 1620 | aaaa                                                              1624

<210> SEQ ID NO 16
<211> LENGTH: 400
<212> TYPE: PRT
<213> ORGANISM: Argemone mexicana

<400> SEQUENCE: 16

Met Ala Leu Lys Leu Asn Pro Leu Thr Phe Gln Ser Gln Lys Phe Pro
 1               5                  10                  15

Cys Phe Gly Phe Pro Asn Val Ala Asn Val Arg Ser Pro Lys Val Phe
                20                  25                  30

Met Ala Ser Thr Leu Arg Ser Ser Ser Lys Glu Thr Glu Lys Leu
            35                  40                  45

Lys Lys Pro Phe Thr Pro Pro Arg Glu Val His Val Gln Val Thr His
        50                  55                  60

Ser Met Pro Pro Gln Lys Ile Glu Ile Phe Lys Ser Leu Glu Asp Trp
 65                  70                  75                  80

Ala Asp Ser Asn Ile Leu Ile His Leu Lys Pro Val Glu Lys Cys Trp
                85                  90                  95

Gln Pro Gln Asp Phe Leu Pro Asp Pro Ala Ser Asp Gly Phe Tyr Asp
                100                 105                 110

Gln Val Lys Glu Leu Arg Glu Arg Ala Lys Glu Ile Pro Asp Glu Tyr
            115                 120                 125

Phe Val Val Leu Val Gly Asp Met Ile Thr Glu Glu Ala Leu Pro Thr
    130                 135                 140

Tyr Gln Thr Met Leu Asn Thr Leu Asp Gly Val Arg Asp Glu Thr Gly
145                 150                 155                 160

Ala Ser Pro Thr Ser Trp Ala Val Trp Thr Arg Ala Trp Thr Ala Glu
                165                 170                 175

Glu Asn Arg His Gly Asp Leu Leu Asn Lys Tyr Leu Tyr Leu Ser Gly
            180                 185                 190

Arg Val Asp Met Lys Gln Ile Glu Lys Thr Ile Gln Tyr Leu Ile Gly
        195                 200                 205

Ser Gly Met Asp Pro Arg Thr Glu Asn Asn Pro Tyr Leu Gly Phe Ile
    210                 215                 220

Tyr Thr Ser Phe Gln Glu Arg Ala Thr Phe Ile Ser His Gly Asn Thr
225                 230                 235                 240

Ala Arg His Ala Lys Glu His Gly Asp Leu Lys Leu Ala Gln Ile Cys
                245                 250                 255

Gly Thr Ile Ala Ala Asp Glu Lys Arg His Glu Thr Ala Tyr Thr Lys
            260                 265                 270

Ile Ser Glu Lys Leu Phe Glu Ile Asp Pro Asp Gly Thr Ile Leu Ala
        275                 280                 285

Phe Ala Asp Met Met Arg Lys Lys Ile Ala Met Pro Ala His Leu Met
    290                 295                 300

Tyr Asp Gly Lys Asp Asp Asn Leu Phe Glu His Phe Ser Ser Val Ala
305                 310                 315                 320

Gln Arg Leu Gly Val Tyr Thr Ala Lys Asp Tyr Ala Asp Ile Leu Glu
                325                 330                 335

Phe Leu Val Ala Arg Trp Asn Val Glu Lys Ile Thr Gly Leu Ser Gly
            340                 345                 350

Glu Gly Arg Lys Ala Gln Asp Tyr Val Cys Gly Leu Thr Pro Arg Ile
        355                 360                 365

```
Arg Arg Leu Glu Glu Arg Ala Gln Ala Gln Ala Lys Lys Asn Lys Gln
    370                 375                 380

Asp Arg His Val Pro Phe Ser Trp Ile Phe Asn Lys Glu Val Leu Leu
385                 390                 395                 400
```

<210> SEQ ID NO 17
<211> LENGTH: 842
<212> TYPE: DNA
<213> ORGANISM: Argemone mexicana

<400> SEQUENCE: 17

```
gcaccagatt ccttcctctt ctccaaaaaa aataaatcaa atctgtttca gtctctcagc      60
tctctctctc tctctctctc tccagtatct tattgggtcg ggaatggatc ctcgaatgga     120
aaacaaccca tatctgggat tcatctacac ctcattccag gagagggcaa ctttcatctc     180
ccacggaaac acggctagac atgcgaagga gcatgggac ttaaaactgg ctcaaatatg      240
tggaaccatt gctgctgatg aaaagcgcca cgaaactgct tattctaaga tcatcgaaaa     300
gctttttgag attgacccag atggtactat cttggccttt gctgatatga tgaggaagaa     360
aattgcaatg ccagcccact taatgtatga cggtagggat gacaatctct ttgagcactt     420
ctcagctgtg gcccaaaggc ttggagttta cacagccaaa gattatgcgg atatattgga     480
atttcttgtg gggagatggg atgtggagaa aataacgggt ctctctggag aaggacggaa     540
agctcaagaa tacgtgtgtg ggttgactcc aaggatcaga aggttggaag atagagctca     600
agctcaagca agaaaaaaca agcaagatcg ccaagttcct ttcagctgga ttttcaataa     660
agaagtgttg ctttaaatag aaattgaaat tatgtttaac tgtgttatat acacactata     720
acaaaaaact tcacatatct cctatctaat aattttagga aatgaatata aaaaaaaaa      780
tcatcatatc aatttgaata tgaatatgaa atgccagaaa attcaaaaaa aaaaaaaaaa     840
aa                                                                   842
```

<210> SEQ ID NO 18
<211> LENGTH: 224
<212> TYPE: PRT
<213> ORGANISM: Argemone mexicana

<400> SEQUENCE: 18

```
His Gln Ile Pro Ser Ser Pro Lys Lys Ile Asn Gln Ile Cys Phe
  1               5                  10                  15

Ser Leu Ser Ala Leu Ser Leu Ser Leu Gln Tyr Leu Ile Gly
                 20                  25                  30

Ser Gly Met Asp Pro Arg Met Glu Asn Asn Pro Tyr Leu Gly Phe Ile
             35                  40                  45

Tyr Thr Ser Phe Gln Glu Arg Ala Thr Phe Ile Ser His Gly Asn Thr
         50                  55                  60

Ala Arg His Ala Lys Glu His Gly Asp Leu Lys Leu Ala Gln Ile Cys
 65                  70                  75                  80

Gly Thr Ile Ala Ala Asp Glu Lys Arg His Glu Thr Ala Tyr Ser Lys
                 85                  90                  95

Ile Ile Glu Lys Leu Phe Glu Ile Asp Pro Asp Gly Thr Ile Leu Ala
                100                 105                 110

Phe Ala Asp Met Met Arg Lys Lys Ile Ala Met Pro Ala His Leu Met
             115                 120                 125

Tyr Asp Gly Arg Asp Asp Asn Leu Phe Glu His Phe Ser Ala Val Ala
        130                 135                 140
```

```
Gln Arg Leu Gly Val Tyr Thr Ala Lys Asp Tyr Ala Asp Ile Leu Glu
145                 150                 155                 160
Phe Leu Val Gly Arg Trp Asp Val Glu Lys Ile Thr Gly Leu Ser Gly
                165                 170                 175
Glu Gly Arg Lys Ala Gln Glu Tyr Val Cys Gly Leu Thr Pro Arg Ile
            180                 185                 190
Arg Arg Leu Glu Asp Arg Ala Gln Ala Gln Ala Lys Lys Asn Lys Gln
        195                 200                 205
Asp Arg Gln Val Pro Phe Ser Trp Ile Phe Asn Lys Glu Val Leu Leu
    210                 215                 220
```

<210> SEQ ID NO 19
<211> LENGTH: 1632
<212> TYPE: DNA
<213> ORGANISM: Oryza sativa

<400> SEQUENCE: 19

| | | | | | |
|---|---|---|---|---|---|
| gcacgagtgt | atcagcagaa | gtccaggtgg | acaagaacgc | gaggagggga | agaatcatcc    60 |
| ccgagatctc | gctgccgctg | ctcatggcgt | tcgcggcgtc | ccacaccgca | tcgccgtcct   120 |
| cctgcggcgg | cgtggcgcag | aggaggagca | atgggatgtc | gccggtggtg | gccatggcct   180 |
| ccaccatcaa | cagggtcaag | actgctaaga | agccctacac | tcctccacgt | gaagttcatc   240 |
| tccaagtcaa | gcattcactg | ccaccccaaa | agcgggagat | tttcgattcg | cttcaacctt   300 |
| gggccaaaga | gaacttttg  | aacctcctga | agccagttga | gaagtcatgg | cagccacagg   360 |
| acttcctgcc | agaccttct  | tccgatgggt | tttatgatga | agtaaaagag | ctgcgggaga   420 |
| gggctaagga | gatccctgat | gactactttg | tttgcttagt | tggagacatg | gttactgagg   480 |
| aagctcttcc | tacctatcaa | acaatgctta | acacccttga | tggtgtccga | gatgaaactg   540 |
| gcgcaagccc | aaccacctgg | gctgtttgga | caagagcatg | gactgctgaa | gagaacaggc   600 |
| atggtgatct | tcttaataag | tacatgtacc | ttactggacg | tgttgacatg | aaacaaattg   660 |
| agaagacaat | acaatacctg | attgggtctg | ggatggatcc | aggaactgag | aataatccct   720 |
| acttgggttt | cctttacaca | tcatttcaag | aaagagctac | atttatatcc | catggcaata   780 |
| ctgcaaggca | cgccaaggag | tacggggacc | ttaagctggc | tcagatatgt | gggacaatag   840 |
| cagctgatga | gaagcgccat | gagacagctt | acaccaagat | agtggagaag | ctcttcgaga   900 |
| ttgatcctga | ctacacagtt | cttgcatttg | ctgacatgat | gaggaagaag | atctcaatgc   960 |
| ctgctcatct | gatgtatgac | ggcaaggacg | acaacttgtt | cgagcatttc | agcgctgtgg  1020 |
| cacagcggct | gggtgtctac | actgcaagag | actatgccga | catcctggag | ttcttggtcc  1080 |
| agaggtggaa | agtcgcagat | ctcaccgggc | tgtccggaga | agggagaagg | gctcaggatt  1140 |
| tcgtctgcac | gttggcgccg | agaatcaggc | ggctggatga | aagagcccaa | gcaagagcta  1200 |
| agcaagcgcc | tgttattcct | ttcagctggg | tttatgaccg | caaagtgcag | ctttgatcat  1260 |
| gatcagtgag | caaccgagac | tgcatcctat | atattggttc | taagatatga | ggttctctat  1320 |
| atggaaaaaa | atctaggtta | tctagctggg | gtagaatgca | attacctgtc | catctgccct  1380 |
| cacaaaatct | gttgtctttt | aagttgataa | cagtgtcgat | gagtctggtg | agaagctgat  1440 |
| gtgagatgca | acagagtgaa | cttatgttgt | attgatgtga | gatgagtatg | gtgacattta  1500 |
| tgtgtacttg | caggttttac | atgacttgta | taagtttaa  | agtaataatg | gagatttgta  1560 |
| tacagacaag | cgtgtgcact | gtcgcatgat | taagtagtct | aaaatccaga | ctaaaaaaaa  1620 |
| aaaaaaaaaa | aa         |            |            |            |             1632 |

```
<210> SEQ ID NO 20
<211> LENGTH: 390
<212> TYPE: PRT
<213> ORGANISM: Oryza sativa

<400> SEQUENCE: 20

Met Ala Phe Ala Ala Ser His Thr Ala Ser Pro Ser Ser Cys Gly Gly
  1               5                  10                  15

Val Ala Gln Arg Arg Ser Asn Gly Met Ser Pro Val Ala Met Ala
                 20                  25                  30

Ser Thr Ile Asn Arg Val Lys Thr Ala Lys Pro Tyr Thr Pro Pro
             35                  40                  45

Arg Glu Val His Leu Gln Val Lys His Ser Leu Pro Pro Gln Lys Arg
         50                  55                  60

Glu Ile Phe Asp Ser Leu Gln Pro Trp Ala Lys Glu Asn Leu Leu Asn
 65                  70                  75                  80

Leu Leu Lys Pro Val Glu Lys Ser Trp Gln Pro Gln Asp Phe Leu Pro
                 85                  90                  95

Asp Pro Ser Ser Asp Gly Phe Tyr Asp Glu Val Lys Glu Leu Arg Glu
                100                 105                 110

Arg Ala Lys Glu Ile Pro Asp Tyr Phe Val Cys Leu Val Gly Asp
            115                 120                 125

Met Val Thr Glu Glu Ala Leu Pro Thr Tyr Gln Thr Met Leu Asn Thr
    130                 135                 140

Leu Asp Gly Val Arg Asp Glu Thr Gly Ala Ser Pro Thr Thr Trp Ala
145                 150                 155                 160

Val Trp Thr Arg Ala Trp Thr Ala Glu Glu Asn Arg His Gly Asp Leu
                165                 170                 175

Leu Asn Lys Tyr Met Tyr Leu Thr Gly Arg Val Asp Met Lys Gln Ile
            180                 185                 190

Glu Lys Thr Ile Gln Tyr Leu Ile Gly Ser Gly Met Asp Pro Gly Thr
        195                 200                 205

Glu Asn Asn Pro Tyr Leu Gly Phe Leu Tyr Thr Ser Phe Gln Glu Arg
    210                 215                 220

Ala Thr Phe Ile Ser His Gly Asn Thr Ala Arg His Ala Lys Glu Tyr
225                 230                 235                 240

Gly Asp Leu Lys Leu Ala Gln Ile Cys Gly Thr Ile Ala Ala Asp Glu
                245                 250                 255

Lys Arg His Glu Thr Ala Tyr Thr Lys Ile Val Glu Lys Leu Phe Glu
            260                 265                 270

Ile Asp Pro Asp Tyr Thr Val Leu Ala Phe Ala Asp Met Met Arg Lys
        275                 280                 285

Lys Ile Ser Met Pro Ala His Leu Met Tyr Asp Gly Lys Asp Asp Asn
    290                 295                 300

Leu Phe Glu His Phe Ser Ala Val Ala Gln Arg Leu Gly Val Tyr Thr
305                 310                 315                 320

Ala Arg Asp Tyr Ala Asp Ile Leu Glu Phe Leu Val Gln Arg Trp Lys
                325                 330                 335

Val Ala Asp Leu Thr Gly Leu Ser Gly Glu Gly Arg Ala Gln Asp
            340                 345                 350

Phe Val Cys Thr Leu Ala Pro Arg Ile Arg Arg Leu Asp Glu Arg Ala
        355                 360                 365

Gln Ala Arg Ala Lys Gln Ala Pro Val Ile Pro Phe Ser Trp Val Tyr
    370                 375                 380
```

-continued

Asp Arg Lys Val Gln Leu
385                 390

<210> SEQ ID NO 21
<211> LENGTH: 645
<212> TYPE: DNA
<213> ORGANISM: Triticum aestivum

<400> SEQUENCE: 21

```
gcgggcaaat gaaatacctg atgaatactt tgtttgctta gttggtgata tggttactga      60
ggaagcctta cctacatacc aaacaatgct taacactctt gatggagtcc gggatgaaac     120
tggtgcaagt ccaaccacgt gggcggtttg dacaagggca tggacagctg aagagaacag     180
acatggtgac ctccttaaca agtacatgta ccttactgga cgggttgaca tgaaacaaat     240
tgagaagacc atacaatatc tgattggttc cggaatggat cctggaactg agaacaaccc     300
ctacttgggt ttcctctaca catcattcca agaaagggca acatttgtgt cgcatgggaa     360
tactgcaagg catgccaagg agtatggtga tctcaagctg gcccagatat gtggcacgat     420
agcagccgat gagaagcgcc acgaaacagc ctacaccaag atagtcgaga agctcttcga     480
gatggaccct gattacacag tgcttgcgtt tgctgacatg atgaggaaga agatcacgat     540
gccagcccat ctcatgtacg acggtaagga cgacaacctg ttcgagcact tcggcgcggt     600
ggcgcagagg ctgggcgtct acaccgccaa agactacgcc gacat                      645
```

<210> SEQ ID NO 22
<211> LENGTH: 214
<212> TYPE: PRT
<213> ORGANISM: Triticum aestivum

<400> SEQUENCE: 22

Arg Ala Asn Glu Ile Pro Asp Glu Tyr Phe Val Cys Leu Val Gly Asp
1               5                   10                  15

Met Val Thr Glu Glu Ala Leu Pro Thr Tyr Gln Thr Met Leu Asn Thr
            20                  25                  30

Leu Asp Gly Val Arg Asp Glu Thr Gly Ala Ser Pro Thr Thr Trp Ala
        35                  40                  45

Val Trp Thr Arg Ala Trp Thr Ala Glu Glu Asn Arg His Gly Asp Leu
    50                  55                  60

Leu Asn Lys Tyr Met Tyr Leu Thr Gly Arg Val Asp Met Lys Gln Ile
65                  70                  75                  80

Glu Lys Thr Ile Gln Tyr Leu Ile Gly Ser Gly Met Asp Pro Gly Thr
                85                  90                  95

Glu Asn Asn Pro Tyr Leu Gly Phe Leu Tyr Thr Ser Phe Gln Glu Arg
            100                 105                 110

Ala Thr Phe Val Ser His Gly Asn Thr Ala Arg His Ala Lys Glu Tyr
        115                 120                 125

Gly Asp Leu Lys Leu Ala Gln Ile Cys Gly Thr Ile Ala Ala Asp Glu
    130                 135                 140

Lys Arg His Glu Thr Ala Tyr Thr Lys Ile Val Glu Lys Leu Phe Glu
145                 150                 155                 160

Met Asp Pro Asp Tyr Thr Val Leu Ala Phe Ala Asp Met Met Arg Lys
                165                 170                 175

Lys Ile Thr Met Pro Ala His Leu Met Tyr Asp Gly Lys Asp Asp Asn
            180                 185                 190

Leu Phe Glu His Phe Gly Ala Val Ala Gln Arg Leu Gly Val Tyr Thr

```
                195                 200                 205
Ala Lys Asp Tyr Ala Asp
    210

<210> SEQ ID NO 23
<211> LENGTH: 1374
<212> TYPE: DNA
<213> ORGANISM: Nicotiana benthamiana

<400> SEQUENCE: 23 ttttttttgct agcaaattga ccaaatgtgg tttcattcca agttgttaca aaacaagagc      60
agaagaaaga agcttcaccc gtgtgctcaa tgtatagtct caccttagtt acattagtag     120
gcaacaagtc acccaaaaat ctcattttca tgtgatacac ttggacgaag ttgaaccgat     180
attgtatttt tcctaactgt cagctaaagc cagcctctgt ttatgagtgt cagttggcaa     240
cctgacatca gtggccaatc caatagcttg aagaaacctt actacatacc aagtcatgtc     300
aagttgccac cattctaagc cgtgcctagc cgaatactcg aacgcatggt ggttattgtg     360
ccaaccttct ccaaatgcaa gcaatgccac ccaccagttg ttccttgaaa ggtcaccagt     420
attccatgcc tgctttcccc aaacgtggca tgctgaattt accagccaag ttatgtggta     480
tacccaaaca attctcaccc ccatgcccca acaatataa ggaaatcctc ccattgcata     540
taacagagct gcaagtgcga caggatggaa acataagtg tcacgaataa actgatagaa     600
gggttgcttc tccaaatccc ccacattgtt gggttttcct gtcctctcaa caatggtgtc     660
tgtatcgaac atccaactca tatgactgaa ccaaaatcct tcaataggac tgtgaggatc     720
tttatcagaa tcacaaaact gatggtggta cctatgagta ctcacccaat caattggatt     780
tccctgaagt gcttgaacac cacaataggc aaaaagatat tctagccatt tgggaagttt     840
gaaacttcta tgagacaaat ttctgtgaaa agaaagagta atacccaaaa gtccagtgat     900
tatatataag ccaaatgcaa ttccaacagc agcccaattg aaggtaaagg gtgctaatag     960
actgagcaaa tgcatacccca caaccacagc agctgagcct acatccactg aattccactg    1020
cctaccaaaa agtacatccc ttggccgctt caccaaaacg tcagaaaaca gaattctgtt    1080
aaagtttgat tttttttccat tttctgatac cggcgaagac gctacattca caattggcat    1140
tactcttctg ttaatcttaa cttttccttc cagtctatag ccattccact tgttaagtag    1200
gcttgttttt gttgttacat tctttgttgg ttgagcaggg aagaagcttc tcgccggcct    1260
atgaattggt tgaggaaggg gcgaaaatgg gtaaggctta aacttggacg gcagtggtgc    1320
aaagagggcc atatttgggc ttggcaatta tttggttgga gttgtttgac ttat           1374

<210> SEQ ID NO 24
<211> LENGTH: 379
<212> TYPE: PRT
<213> ORGANISM: Nicotiana benthamiana

<400> SEQUENCE: 24

Met Ala Leu Phe Ala Pro Leu Pro Ser Lys Phe Lys Pro Tyr Pro Phe
  1               5                  10                  15

Ser Pro Leu Pro Gln Pro Ile His Arg Pro Ala Arg Ser Phe Phe Pro
            20                  25                  30

Ala Gln Pro Thr Lys Asn Val Thr Thr Lys Thr Ser Leu Leu Asn Lys
        35                  40                  45

Trp Asn Gly Tyr Arg Leu Glu Gly Lys Val Lys Ile Asn Arg Arg Val
    50                  55                  60
```

```
Met Pro Ile Val Asn Val Ala Ser Ser Pro Val Ser Glu Asn Gly Lys
 65                  70                  75                  80

Lys Ser Asn Phe Asn Arg Ile Leu Phe Ser Asp Val Leu Val Lys Arg
                 85                  90                  95

Pro Arg Asp Val Leu Phe Gly Arg Gln Trp Asn Ser Val Asp Val Gly
            100                 105                 110

Ser Ala Ala Val Val Gly Met His Leu Leu Ser Leu Leu Ala Pro
        115                 120                 125

Phe Thr Phe Asn Trp Ala Ala Val Gly Ile Ala Phe Gly Leu Tyr Ile
    130                 135                 140

Ile Thr Gly Leu Leu Gly Ile Thr Leu Ser Phe His Arg Asn Leu Ser
145                 150                 155                 160

His Arg Ser Phe Lys Leu Pro Lys Trp Leu Glu Tyr Leu Phe Ala Tyr
                165                 170                 175

Cys Gly Val Gln Ala Leu Gln Gly Asn Pro Ile Asp Trp Val Ser Thr
            180                 185                 190

His Arg Tyr His His Gln Phe Cys Asp Ser Asp Lys Asp Pro His Ser
        195                 200                 205

Pro Ile Glu Gly Phe Trp Phe Ser His Met Ser Trp Met Phe Asp Thr
    210                 215                 220

Asp Thr Ile Val Glu Arg Thr Gly Lys Pro Asn Asn Val Gly Asp Leu
225                 230                 235                 240

Glu Lys Gln Pro Phe Tyr Gln Phe Ile Arg Asp Thr Tyr Val Phe His
                245                 250                 255

Pro Val Ala Leu Ala Ala Leu Leu Tyr Ala Met Gly Gly Phe Pro Tyr
            260                 265                 270

Ile Val Trp Gly Met Gly Val Arg Ile Val Trp Val Tyr His Ile Thr
        275                 280                 285

Trp Leu Val Asn Ser Ala Cys His Val Trp Gly Lys Gln Ala Trp Asn
    290                 295                 300

Thr Gly Asp Leu Ser Arg Asn Asn Trp Trp Val Ala Leu Leu Ala Phe
305                 310                 315                 320

Gly Glu Gly Trp His Asn Asn His His Ala Phe Glu Tyr Ser Ala Arg
                325                 330                 335

His Gly Leu Glu Trp Trp Gln Leu Asp Met Thr Trp Tyr Val Val Arg
            340                 345                 350

Phe Leu Gln Ala Ile Gly Leu Ala Thr Asp Val Arg Leu Pro Thr Asp
        355                 360                 365

Thr His Lys Gln Arg Leu Ala Leu Ala Asp Ser
370                 375

<210> SEQ ID NO 25
<211> LENGTH: 396
<212> TYPE: DNA
<213> ORGANISM: Arabidopsis thaliana
<220> FEATURE:
<221> NAME/KEY: unsure
<222> LOCATION: (352)
<223> OTHER INFORMATION: n is a, c, g or t
<220> FEATURE:
<221> NAME/KEY: unsure
<222> LOCATION: (363)
<223> OTHER INFORMATION: n is a, c, g or t
<220> FEATURE:
<221> NAME/KEY: unsure
<222> LOCATION: (373)
<223> OTHER INFORMATION: n is a, c, g or t
<220> FEATURE:
<221> NAME/KEY: unsure
```

```
<222> LOCATION: (376)
<223> OTHER INFORMATION: n is a, c, g or t
<220> FEATURE:
<221> NAME/KEY: unsure
<222> LOCATION: (378)
<223> OTHER INFORMATION: n is a, c, g or t
<220> FEATURE:
<221> NAME/KEY: unsure
<222> LOCATION: (383)
<223> OTHER INFORMATION: n is a, c, g or t

<400> SEQUENCE: 25
gtcgtaagag cgtcagtcgt tgtgattgtg cactttttgt gtctcttggc gccgtttaac      60
ttcaaatggg aagctttacg gttcggtttg gtgctcttcg cgttgactac actcagcatc    120
acattctcat tccataggaa cttgtctcac cgtagcttca agataccaaa atggctcgaa    180
tatccttggg cttattctgc tgttttcgct cttcagggtg attcaatgga ttgggtgagc    240
atacataggt tccatcaaca gttcacagat tcggaccgcg acccacatag cccctaaaga    300
aggattattg ttcaagccat atcttgtgga tatttgacac ccaaatacat cnaatacaaa    360
gtngtggggg acntgncnac ctnttgggcc tttcaa                              396

<210> SEQ ID NO 26
<211> LENGTH: 98
<212> TYPE: PRT
<213> ORGANISM: Arabidopsis thaliana

<400> SEQUENCE: 26
```

Val Val Arg Ala Ser Val Val Ile Val His Phe Leu Cys Leu Leu
1               5                   10                  15

Ala Pro Phe Asn Phe Lys Trp Glu Ala Leu Arg Phe Gly Leu Val Leu
            20                  25                  30

Phe Ala Leu Thr Thr Leu Ser Ile Thr Phe Ser Phe His Arg Asn Leu
        35                  40                  45

Ser His Arg Ser Phe Lys Ile Pro Lys Trp Leu Glu Tyr Pro Trp Ala
    50                  55                  60

Tyr Ser Ala Val Phe Ala Leu Gln Gly Asp Ser Met Asp Trp Val Ser
65                  70                  75                  80

Ile His Arg Phe His Gln Gln Phe Thr Asp Ser Asp Arg Asp Pro His
                85                  90                  95

Ser Pro

```
<210> SEQ ID NO 27
<211> LENGTH: 398
<212> TYPE: DNA
<213> ORGANISM: Arabidopsis thaliana

<400> SEQUENCE: 27
atggcttctc ttctaacaaa acccaaaccc gttttcctct gttcaccatc gttatctcca      60
agaactttga acacagcaac accgtcattg aatttcacca gaatttcatt cacccatcac    120
caaaagcttg ctcctttcaa gcctcctagt ctcgttgttg cattctctga aaagggtttg    180
aagagagatg tcaccacagc tgctgcagcg acggagggag attacagaag gataatgtta    240
tctgatgtgt tggtgaagaa gaaggaaaaa gtagtttggt gggagagaga atggaaagct    300
atggactttg gagctgttgc tgtcgttttg tctatgcatt tgcttagtct tttggctccg    360
tttcaattca attggagagc tgtttcgggt gcttttgg                            398

<210> SEQ ID NO 28
```

-continued

```
<211> LENGTH: 132
<212> TYPE: PRT
<213> ORGANISM: Arabidopsis thaliana

<400> SEQUENCE: 28

Met Ala Ser Leu Leu Thr Lys Pro Lys Pro Val Phe Leu Cys Ser Pro
 1               5                  10                  15

Ser Leu Ser Pro Arg Thr Leu Asn Thr Ala Thr Pro Ser Leu Asn Phe
            20                  25                  30

Thr Arg Ile Ser Phe Thr His His Gln Lys Leu Ala Pro Phe Lys Pro
        35                  40                  45

Pro Ser Leu Val Val Ala Phe Ser Glu Lys Gly Leu Lys Arg Asp Val
    50                  55                  60

Thr Thr Ala Ala Ala Thr Glu Gly Asp Tyr Arg Arg Ile Met Leu
65                  70                  75                  80

Ser Asp Val Leu Val Lys Lys Glu Lys Val Val Trp Trp Glu Arg
                85                  90                  95

Glu Trp Lys Ala Met Asp Phe Gly Ala Val Ala Val Leu Ser Met
            100                 105                 110

His Leu Leu Ser Leu Leu Ala Pro Phe Gln Phe Asn Trp Arg Ala Val
            115                 120                 125

Ser Gly Ala Phe
    130

<210> SEQ ID NO 29
<211> LENGTH: 461
<212> TYPE: DNA
<213> ORGANISM: Alstroemeria caryophylla
<220> FEATURE:
<221> NAME/KEY: unsure
<222> LOCATION: (447)
<223> OTHER INFORMATION: n is a, c, g or t

<400> SEQUENCE: 29
agatgatggc tctgctgctg aagcccaacc tcagcctcta ccaagctccc aagctccccc      60
gcctcccatt ccgtctctcc accccctcc acccgggcct caccggacga cccatctcca     120
accccactgt tctaagggcc aggggaggca atgcagccgc gctctgctgc ctctccggcg     180
aggtcgcaac caagagaata ctctggtccg acgtggaggt gaagcagccg gcgagggtgt     240
acttcgggcg taagtggaac ttgcccgacg tcgcgtcggc cggggttgtc ctctccaccc     300
acctcctctc cttgctggcg cccttcacct tcacctgggc ggcgctctgg accgcggcgg     360
cgctctacat agtgacgggc ctgctgggcg tcacgctctc cttccaacga aacctcgccc     420
aacgcagctt ctccctcccc aaatggntcg aagtactcct t                         461

<210> SEQ ID NO 30
<211> LENGTH: 153
<212> TYPE: PRT
<213> ORGANISM: Alstroemeria caryophylla
<220> FEATURE:
<221> NAME/KEY: UNSURE
<222> LOCATION: (149)
<223> OTHER INFORMATION: Xaa can be any naturally occurring amino acid

<400> SEQUENCE: 30

Met Met Ala Leu Leu Leu Lys Pro Asn Leu Ser Leu Tyr Gln Ala Pro
 1               5                  10                  15

Lys Leu Pro Arg Leu Pro Phe Arg Leu Ser Thr Thr Leu His Pro Gly
            20                  25                  30
```

-continued

```
Leu Thr Gly Arg Pro Ile Ser Asn Pro Thr Val Leu Arg Ala Arg Gly
             35                  40                  45

Gly Asn Ala Ala Ala Leu Cys Cys Leu Ser Gly Glu Val Ala Thr Lys
     50                  55                  60

Arg Ile Leu Trp Ser Asp Val Glu Val Lys Gln Pro Ala Arg Val Tyr
 65                  70                  75                  80

Phe Gly Arg Lys Trp Asn Leu Pro Asp Val Ala Ser Ala Gly Val Val
                 85                  90                  95

Leu Ser Thr His Leu Leu Ser Leu Leu Ala Pro Phe Thr Phe Thr Trp
            100                 105                 110

Ala Ala Leu Trp Thr Ala Ala Leu Tyr Ile Val Thr Gly Leu Leu
        115                 120                 125

Gly Val Thr Leu Ser Phe Gln Arg Asn Leu Ala Gln Arg Ser Phe Ser
    130                 135                 140

Leu Pro Lys Trp Xaa Glu Val Leu Leu
145                 150
```

<210> SEQ ID NO 31
<211> LENGTH: 448
<212> TYPE: DNA
<213> ORGANISM: Calendula officinalis

<400> SEQUENCE: 31

```
gtggcataca taaacatatc aaattgtgta ccatacaaga atgtcttcgg atggttcaaa    60
ggaattaaaa cataggagaa taattttctc cgatgtggag gtgatcagga aaagaaacct   120
cttccgcggt cgtaaatgga ggtccctcga cattaaaatg gcctcgggaa ttttgttttt   180
ccatgttttg gcactctttg caccatttac attcacttgg gatgcttttt tgctagcatt   240
tttgtgttac ttttaattg ggattttggg gataaccatg tgttaccata ggcttttagc    300
acaccgtagt ctcaagctac ccaaatggct cgagtacaca tgtgcttatt taggggttca   360
agctatacaa agggatccga tatattgggt gagcatccaa agggtatcaa caacaatacg   420
ttgaatcgga gaacgatcac atacgccc                                       448
```

<210> SEQ ID NO 32
<211> LENGTH: 310
<212> TYPE: PRT
<213> ORGANISM: Calendula officinalis

<400> SEQUENCE: 32

```
Met Ser Ser Asp Gly Ser Lys Glu Leu Lys His Arg Arg Ile Ile Phe
  1               5                  10                  15

Ser Asp Val Glu Val Ile Arg Lys Arg Asn Leu Phe Arg Gly Arg Lys
                 20                  25                  30

Trp Arg Ser Leu Asp Ile Lys Met Ala Ser Gly Ile Leu Phe Phe His
             35                  40                  45

Val Leu Ala Leu Phe Ala Pro Phe Thr Phe Thr Trp Asp Ala Phe Leu
 50                  55                  60

Leu Ala Phe Leu Cys Tyr Phe Leu Ile Gly Ile Leu Gly Ile Thr Met
 65                  70                  75                  80

Cys Tyr His Arg Leu Leu Ala His Arg Ser Leu Lys Leu Pro Lys Trp
                 85                  90                  95

Leu Glu Tyr Thr Cys Ala Tyr Leu Gly Val Gln Ala Ile Gln Arg Asp
            100                 105                 110

Pro Ile Tyr Trp Val Ser Ile His Arg Tyr His His Gln Tyr Val Glu
        115                 120                 125
```

```
Ser Glu Asn Asp Pro His Thr Pro Thr Phe Gly Phe Trp Phe Ser His
    130                 135                 140

Met Gly Trp Leu Phe Asp Ser Gly Phe Ile Met Glu Lys Tyr Gln Glu
145                 150                 155                 160

Arg Arg Asn Val Glu Asp Leu Lys Ser Gln Ala Phe Tyr Met Phe Ile
                165                 170                 175

Lys Arg Thr Tyr Leu Trp His Ile Phe Gly Phe Gly Val Leu Val Tyr
            180                 185                 190

Ala Trp Gly Gly Phe Pro Tyr Leu Val Trp Ile Val Gly Val Arg Asn
            195                 200                 205

Val Trp Gly Leu Gln Val Thr Phe Leu Val Asn Ser Ala Cys His Ile
    210                 215                 220

Trp Gly Lys Arg Ala Trp Asn Thr Asp Asp Leu Ser Arg Asn Asn Trp
225                 230                 235                 240

Trp Val Ala Leu Val Thr Phe Gly Glu Gly Trp His Asn Asn His His
                245                 250                 255

Ala Phe Glu Tyr Ser Ala Arg His Gly Leu Glu Trp Trp Gln Ile Asp
            260                 265                 270

Leu Cys Trp Tyr Met Ile Arg Phe Leu Gln Ser Ile Gly Leu Ala Thr
            275                 280                 285

Asn Val Lys Leu Pro Thr Gln Asp His Lys Leu Lys Ser Phe Gly
    290                 295                 300

Ser Asn Ser Lys Phe Arg
305                 310
```

<210> SEQ ID NO 33
<211> LENGTH: 1166
<212> TYPE: DNA
<213> ORGANISM: Calendula officinalis

<400> SEQUENCE: 33

```
ctgcaggaat tcggcacgag gccatgtcac cggccaacta tgacaagtct ccggtaacaa     60
acaaccaaat acgaggacc  aacgtggtc  ctggttatag tcctgacgac gaccaaaaga    120
agacccaact gtcgtcggag ttggagaaaa ggaggaaagg agggttttgg ctccggagat    180
ggagcttggc tgacgtggct acccttttgct ggatcgtcga gatacacatg ttggctgcat   240
gcgcaccttt tgtattcgat tggggtgcat tcactgtggc tatggggttg gcattgttga    300
ccggaatggg tatgacactc gggtatcata gacttcttac tcaccggagt ttcaagattc    360
caaaatggct cgaatatttc tttgcttaca gtggtgttct cgccggacag aaagatccaa    420
tatcttgggt gagcacacac aagagtcacc acaagtattc tgacacagac agggaccctc    480
attctccaac cgaaggttt  tggtttagtc atataggttg gttctgttac agcgattaca    540
tagctgcaaa gtgtggagga gaatactcga atgtacctga gctaaaggca caatggttct    600
ataggtttct tcatgatact tactttttgtc atccaattac actcgcaata atattatatc    660
tctatggaga ctttccctac ttggcttggg gattgggcat acgagcaacg ttggtttgcc    720
acatcacgtt tgtcgtgcgc tccgtcgggc atatatgggg tgataggtct tggaatacaa    780
ttgatacttc cacaaataac tggtggacag gtgcgatatc tttaggagaa ggttggcata    840
acaatcacca tgctttccca aattcggctc gacatggatt ggaatggtgg caagtggact    900
tgacatggga gttgatcaag tttcttgagt tagttggatt agcaacggat gttaagttac    960
ccaccgaggc tgaaataaga agaatcgcat cgttgggctc aaagtcttga tcacgatggt   1020
```

-continued

```
tacttaaata ctcactttt ccaaactctg cctctagcta gctagattgg ttattattgt    1080
tgttgaataa agatcaaatc gtttatcttg ctatcatgtg gtacattata tatttataga   1140
atttatattg ctaaaaaaaa aaaaag                                        1166
```

<210> SEQ ID NO 34
<211> LENGTH: 328
<212> TYPE: PRT
<213> ORGANISM: Calendula officinalis

<400> SEQUENCE: 34

```
Met Ser Pro Ala Asn Tyr Asp Lys Ser Pro Val Thr Asn Asn Gln Ile
  1               5                  10                  15

Arg Arg Thr Asn Gly Gly Pro Gly Tyr Ser Pro Asp Asp Gln Lys
             20                  25                  30

Lys Thr Gln Leu Ser Ser Glu Leu Glu Lys Arg Arg Lys Gly Gly Phe
         35                  40                  45

Trp Leu Arg Arg Trp Ser Leu Ala Asp Val Ala Thr Leu Cys Trp Ile
     50                  55                  60

Val Glu Ile His Met Leu Ala Ala Cys Ala Pro Phe Val Phe Asp Trp
 65                  70                  75                  80

Gly Ala Phe Thr Val Ala Met Gly Leu Ala Leu Leu Thr Gly Met Gly
                 85                  90                  95

Met Thr Leu Gly Tyr His Arg Leu Leu Thr His Arg Ser Phe Lys Ile
            100                 105                 110

Pro Lys Trp Leu Glu Tyr Phe Phe Ala Tyr Ser Gly Val Leu Ala Gly
        115                 120                 125

Gln Lys Asp Pro Ile Ser Trp Val Ser Thr His Lys Ser His His Lys
    130                 135                 140

Tyr Ser Asp Thr Asp Arg Asp Pro His Ser Pro Thr Glu Gly Phe Trp
145                 150                 155                 160

Phe Ser His Ile Gly Trp Phe Cys Tyr Ser Asp Tyr Ile Ala Ala Lys
                165                 170                 175

Cys Gly Gly Glu Tyr Ser Asn Val Pro Glu Leu Lys Ala Gln Trp Phe
            180                 185                 190

Tyr Arg Phe Leu His Asp Thr Tyr Phe Cys His Pro Ile Thr Leu Ala
        195                 200                 205

Ile Ile Leu Tyr Leu Tyr Gly Asp Phe Pro Tyr Leu Ala Trp Gly Leu
    210                 215                 220

Gly Ile Arg Ala Thr Leu Val Cys His Ile Thr Phe Val Val Arg Ser
225                 230                 235                 240

Val Gly His Ile Trp Gly Asp Arg Ser Trp Asn Thr Ile Asp Thr Ser
                245                 250                 255

Thr Asn Asn Trp Trp Thr Gly Ala Ile Ser Leu Gly Glu Gly Trp His
            260                 265                 270

Asn His His Ala Phe Pro Asn Ser Ala Arg His Gly Leu Glu Trp
        275                 280                 285

Trp Gln Val Asp Leu Thr Trp Glu Leu Ile Lys Phe Leu Glu Leu Val
    290                 295                 300

Gly Leu Ala Thr Asp Val Lys Leu Pro Thr Glu Ala Glu Ile Arg Arg
305                 310                 315                 320

Ile Ala Ser Leu Gly Ser Lys Ser
                325
```

<210> SEQ ID NO 35

```
<211> LENGTH: 535
<212> TYPE: DNA
<213> ORGANISM: Oryza sativa
<220> FEATURE:
<221> NAME/KEY: unsure
<222> LOCATION: (167)
<223> OTHER INFORMATION: n is a, c, g or t
<220> FEATURE:
<221> NAME/KEY: unsure
<222> LOCATION: (214)
<223> OTHER INFORMATION: n is a, c, g or t
<220> FEATURE:
<221> NAME/KEY: unsure
<222> LOCATION: (287)
<223> OTHER INFORMATION: n is a, c, g or t
<220> FEATURE:
<221> NAME/KEY: unsure
<222> LOCATION: (294)
<223> OTHER INFORMATION: n is a, c, g or t
<220> FEATURE:
<221> NAME/KEY: unsure
<222> LOCATION: (316)
<223> OTHER INFORMATION: n is a, c, g or t
<220> FEATURE:
<221> NAME/KEY: unsure
<222> LOCATION: (323)
<223> OTHER INFORMATION: n is a, c, g or t
<220> FEATURE:
<221> NAME/KEY: unsure
<222> LOCATION: (326)
<223> OTHER INFORMATION: n is a, c, g or t
<220> FEATURE:
<221> NAME/KEY: unsure
<222> LOCATION: (330)
<223> OTHER INFORMATION: n is a, c, g or t
<220> FEATURE:
<221> NAME/KEY: unsure
<222> LOCATION: (336)
<223> OTHER INFORMATION: n is a, c, g or t
<220> FEATURE:
<221> NAME/KEY: unsure
<222> LOCATION: (366)
<223> OTHER INFORMATION: n is a, c, g or t
<220> FEATURE:
<221> NAME/KEY: unsure
<222> LOCATION: (386)
<223> OTHER INFORMATION: n is a, c, g or t
<220> FEATURE:
<221> NAME/KEY: unsure
<222> LOCATION: (389)
<223> OTHER INFORMATION: n is a, c, g or t
<220> FEATURE:
<221> NAME/KEY: unsure
<222> LOCATION: (399)
<223> OTHER INFORMATION: n is a, c, g or t
<220> FEATURE:
<221> NAME/KEY: unsure
<222> LOCATION: (408)
<223> OTHER INFORMATION: n is a, c, g or t
<220> FEATURE:
<221> NAME/KEY: unsure
<222> LOCATION: (411)
<223> OTHER INFORMATION: n is a, c, g or t
<220> FEATURE:
<221> NAME/KEY: unsure
<222> LOCATION: (419)
<223> OTHER INFORMATION: n is a, c, g or t
<220> FEATURE:
<221> NAME/KEY: unsure
<222> LOCATION: (427)
<223> OTHER INFORMATION: n is a, c, g or t
<220> FEATURE:
<221> NAME/KEY: unsure
<222> LOCATION: (429)
<223> OTHER INFORMATION: n is a, c, g or t
<220> FEATURE:
<221> NAME/KEY: unsure
<222> LOCATION: (431)
<223> OTHER INFORMATION: n is a, c, g or t
```

```
<220> FEATURE:
<221> NAME/KEY: unsure
<222> LOCATION: (448)
<223> OTHER INFORMATION: n is a, c, g or t
<220> FEATURE:
<221> NAME/KEY: unsure
<222> LOCATION: (498)
<223> OTHER INFORMATION: n is a, c, g or t
<220> FEATURE:
<221> NAME/KEY: unsure
<222> LOCATION: (508)
<223> OTHER INFORMATION: n is a, c, g or t
<220> FEATURE:
<221> NAME/KEY: unsure
<222> LOCATION: (515)
<223> OTHER INFORMATION: n is a, c, g or t
<220> FEATURE:
<221> NAME/KEY: unsure
<222> LOCATION: (518)
<223> OTHER INFORMATION: n is a, c, g or t
<220> FEATURE:
<221> NAME/KEY: unsure
<222> LOCATION: (526)
<223> OTHER INFORMATION: n is a, c, g or t

<400> SEQUENCE: 35
gtgggcggtc aactcggtgt cgcacgtgtg gggcaaccag acgtacaaca cgggcgacct      60
gtcgcgcaac aactggctca ttggcatcct gggcctgggg cgagggctgg cacaacaacc     120
accacgcatt tgtgttctcg gcgcgccacg gcctggagcc acaccangtg gacgttgacg     180
tggggcatca tttgggcgct ggagaaaact gggnctggcc aacaacgtca agctgcctac     240
ggagaaacaa aaaggtaaag ctccccttcc ccacttgaca aagcccnatc cgcnggccta     300
aaagcaagcc acctcngttc ggncgnttgn catgtggag ggaatccgcg cctgttgagc      360
cgtaancgca aaccggcgca aagggncgng ttttgttgnc ccgggccnga ngttttttna     420
agccccngng nggcaacaat ttttcctnaa aaagtgcgcc gggggtgcaa aggtcctgct     480 ttaaaagga tcttgggntg ggggcaancc cggtngtngg gtgggntcct gtttg           535

<210> SEQ ID NO 36
<211> LENGTH: 52
<212> TYPE: PRT
<213> ORGANISM: Oryza sativa

<400> SEQUENCE: 36

Trp Ala Val Asn Ser Val Ser His Val Trp Gly Asn Gln Thr Tyr Asn
  1               5                  10                  15

Thr Gly Asp Leu Ser Arg Asn Asn Trp Leu Ile Gly Ile Leu Ala Trp
             20                  25                  30

Gly Glu Gly Trp His Asn Asn His His Ala Phe Val Phe Ser Ala Arg
         35                  40                  45

His Gly Leu Glu
         50

<210> SEQ ID NO 37
<211> LENGTH: 532
<212> TYPE: DNA
<213> ORGANISM: Glycine max
<220> FEATURE:
<221> NAME/KEY: unsure
<222> LOCATION: (15)
<223> OTHER INFORMATION: n is a, c, g or t
<220> FEATURE:
<221> NAME/KEY: unsure
<222> LOCATION: (40)
<223> OTHER INFORMATION: n is a, c, g or t
```

<400> SEQUENCE: 37

```
cccccatgct tttgngtacc tcatttagac ttggacttgn gtggtgccat ttagacttga    60
cttggtactt tgtgagattt ccccaagcta ttggtttgcc cactgacgtc aagttaccca   120
cagagagtca gacgcagaaa atggcattcc tttagtgact caattgccac gtgaaacaca   180
ataaatgata aaaaaaaaat gtgaaaataa aaaggatttt agaggtactc gttgatggca   240
caaaagtttt ggtagggaaa ttgttctttt ttgggtctta ctttcagcca tcatcgatgc   300
tggatttgac catgtatatg ggactagaaa ataatgttac tatatattga cacacaagaa   360
tatttaatta ttatccttgc atcttccttt agttattatc ttattatact gtgattgaaa   420
gtcagtcatt gagcttcaat gagaatcaat tttaaaattt cgtacatact atctaaactc   480
tcttaggatc tgttcggtag aatagaataa aaaaaattga gatgtaagtt tt           532
```

<210> SEQ ID NO 38
<211> LENGTH: 45
<212> TYPE: PRT
<213> ORGANISM: Glycine max
<220> FEATURE:
<221> NAME/KEY: UNSURE
<222> LOCATION: (8)
<223> OTHER INFORMATION: Xaa can be any naturally occurring amino acid

<400> SEQUENCE: 38

```
Thr Ser Phe Arg Leu Gly Leu Xaa Trp Cys His Leu Asp Leu Thr Trp
  1               5                  10                  15
Tyr Phe Val Arg Phe Pro Gln Ala Ile Gly Leu Pro Thr Asp Val Lys
             20                  25                  30
Leu Pro Thr Glu Ser Gln Thr Gln Lys Met Ala Phe Leu
         35                  40                  45
```

<210> SEQ ID NO 39
<211> LENGTH: 311
<212> TYPE: DNA
<213> ORGANISM: Vitis sp.
<220> FEATURE:
<221> NAME/KEY: unsure
<222> LOCATION: (286)
<223> OTHER INFORMATION: n is a, c, g or t
<220> FEATURE:
<221> NAME/KEY: unsure
<222> LOCATION: (303)..(304)
<223> OTHER INFORMATION: n is a, c, g or t

<400> SEQUENCE: 39

```
agagggtgg cacaataatc accatgcttt tgaatactcc gctcgtcatg gcctggaatg     60
gtggcaaatt gatatgactt ggtacgtggt taggttcctt caagctcttg gattggcaac   120
cgatgtcaaa ttaccaactg agcttcataa gcaacggatg gctttcaaca actcaactct   180
gctcacatga agattgtctc tgaaactgtc gctgcaacac ttttactctt tgctgaaat    240
tcaagcccat atggtttatt aaacttcaaa ctaaataata aatacnaacc cttttttgccc  300
aannaaaaaa a                                                        311
```

<210> SEQ ID NO 40
<211> LENGTH: 54
<212> TYPE: PRT
<213> ORGANISM: Vitis sp.

<400> SEQUENCE: 40

```
Glu Gly Trp His Asn Asn His His Ala Phe Glu Tyr Ser Ala Arg His
  1               5                  10                  15
```

-continued

```
Gly Leu Glu Trp Trp Gln Ile Asp Met Thr Trp Tyr Val Val Arg Phe
                 20                  25                  30

Leu Gln Ala Leu Gly Leu Ala Thr Asp Val Lys Leu Pro Thr Glu Leu
         35                  40                  45

His Lys Gln Arg Met Ala
         50

<210> SEQ ID NO 41
<211> LENGTH: 390
<212> TYPE: PRT
<213> ORGANISM: Oryza sativa

<400> SEQUENCE: 41

Met Ala Phe Ala Ala Ser His Thr Ala Ser Pro Tyr Ser Cys Gly Gly
  1               5                  10                  15

Val Ala Gln Arg Arg Ser Asn Gly Met Ser Lys Met Val Ala Met Ala
                 20                  25                  30

Ser Thr Ile Asn Arg Val Lys Thr Ala Lys Lys Pro Tyr Thr Pro Pro
         35                  40                  45

Arg Glu Val His Leu Gln Val Lys His Ser Leu Pro Pro Gln Lys Arg
     50                  55                  60

Glu Ile Phe Asp Ser Leu Gln Pro Trp Ala Lys Glu Asn Leu Leu Asn
 65                  70                  75                  80

Leu Leu Lys Pro Val Glu Lys Ser Trp Gln Pro Gln Asp Phe Leu Pro
                 85                  90                  95

Asp Pro Ser Ser Asp Gly Phe Tyr Asp Glu Val Lys Glu Leu Arg Glu
                100                 105                 110

Arg Ala Lys Glu Ile Pro Asp Asp Tyr Phe Val Cys Leu Val Gly Asp
                115                 120                 125

Met Val Thr Glu Glu Ala Leu Pro Thr Tyr Gln Thr Met Leu Asn Thr
            130                 135                 140

Leu Asp Gly Val Arg Asp Glu Thr Gly Ala Ser Pro Thr Thr Trp Ala
145                 150                 155                 160

Val Trp Thr Arg Ala Trp Thr Ala Glu Glu Asn Arg His Gly Asp Leu
                165                 170                 175

Leu Asn Lys Tyr Met Tyr Leu Thr Gly Arg Val Asp Met Lys Gln Ile
                180                 185                 190

Glu Lys Thr Ile Gln Tyr Leu Ile Gly Ser Gly Met Asp Pro Gly Thr
            195                 200                 205

Glu Asn Asn Pro Tyr Leu Gly Phe Leu Tyr Thr Ser Phe Gln Glu Arg
        210                 215                 220

Ala Thr Phe Ile Ser His Gly Asn Thr Ala Arg His Ala Lys Glu Tyr
225                 230                 235                 240

Gly Asp Leu Lys Leu Ala Gln Ile Cys Gly Thr Ile Ala Ala Asp Glu
                245                 250                 255

Lys Arg His Glu Thr Ala Tyr Thr Lys Ile Val Glu Lys Leu Phe Glu
                260                 265                 270

Ile Asp Pro Asp Tyr Thr Val Leu Ala Phe Ala Asp Met Met Arg Asn
            275                 280                 285

Lys Ile Ser Met Thr Ala His Leu Met Tyr Asp Gly Lys Asp Asp Asn
        290                 295                 300

Leu Phe Glu His Leu Ser Ala Val Ala Gln Arg Leu Gly Val Tyr Thr
305                 310                 315                 320

Val Arg Asp Tyr Ala Asp Met Leu Glu Phe Leu Val Gln Arg Trp Lys
```

```
                      325                 330                 335
Val Ala Asp Leu Thr Gly Leu Ser Gly Glu Gly Arg Arg Ala Gln Asp
                340                 345                 350

Phe Val Cys Thr Leu Ala Pro Arg Ile Arg Arg Leu Asp Glu Arg Ala
            355                 360                 365

Gln Ala Arg Ala Lys Gln Ala Pro Val Ile Pro Phe Ser Trp Val Tyr
        370                 375                 380

Asp Arg Lys Val Gln Leu
385                 390

<210> SEQ ID NO 42
<211> LENGTH: 396
<212> TYPE: PRT
<213> ORGANISM: Sesamum indicum

<400> SEQUENCE: 42

Met Ala Leu Lys Leu Asn Ala Ile Asn Phe Gln Ser Pro Lys Cys Pro
 1               5                  10                  15

Ser Phe Ala Leu Pro Pro Val Ala Ser Val Arg Ser Pro Lys Phe Phe
                20                  25                  30

Met Ala Ser Thr Leu Arg Ser Gly Ser Lys Glu Val Glu Thr Val Lys
            35                  40                  45

Arg Pro Phe Asn Pro Pro Arg Glu Val His Val Gln Val Thr His Ser
        50                  55                  60

Met Pro Pro Gln Lys Ile Glu Ile Phe Lys Ala Leu Glu Asp Trp Ala
65                  70                  75                  80

Asp Asn Asn Ile Leu Val His Leu Lys Pro Val Glu Lys Cys Trp Gln
                85                  90                  95

Pro Gln Asp Phe Leu Pro Asp Pro Ser Ser Asp Gly Phe Asp Asp Gln
            100                 105                 110

Val Lys Glu Leu Arg Glu Arg Ala Lys Glu Ile Pro Asp Asp Tyr Phe
        115                 120                 125

Val Val Leu Val Gly Asp Met Ile Thr Glu Glu Ala Leu Pro Thr Tyr
    130                 135                 140

Gln Thr Met Leu Asn Thr Leu Asp Gly Val Arg Asp Glu Thr Gly Ala
145                 150                 155                 160

Ser Pro Thr Ser Trp Ala Ile Trp Thr Arg Ala Trp Thr Ala Glu Glu
                165                 170                 175

Asn Arg His Gly Asp Leu Leu Asn Lys Tyr Leu Tyr Leu Ser Gly Arg
            180                 185                 190

Val Asp Met Arg Gln Ile Glu Lys Thr Ile Gln Tyr Leu Ile Gly Ser
        195                 200                 205

Gly Met Asp Pro Arg Thr Glu Asn Ser Pro Tyr Leu Gly Phe Ile Tyr
    210                 215                 220

Thr Ser Phe Gln Glu Arg Ala Thr Phe Ile Ser His Gly Asn Thr Ala
225                 230                 235                 240

Arg Leu Ala Arg Glu His Gly Asp Leu Lys Leu Ala Gln Ile Cys Gly
                245                 250                 255

Thr Ile Ala Ala Asp Glu Lys Arg His Glu Thr Ala Tyr Thr Lys Ile
            260                 265                 270

Val Glu Lys Leu Phe Glu Ile Asp Pro Asn Asp Thr Val Leu Ala Phe
        275                 280                 285

Ala Asp Met Met Arg Lys Lys Ile Ser Met Pro Ala His Leu Met Tyr
    290                 295                 300
```

```
Asp Gly Arg Asp Asp Asn Leu Phe Asp His Phe Ser Ser Val Ala Gln
305                 310                 315                 320

Arg Leu Gly Val Tyr Thr Ala Lys Asp Tyr Ala Asp Ile Leu Glu His
            325                 330                 335

Leu Val Ala Arg Trp Lys Val Ala Asn Leu Thr Gly Leu Ser Ala Asp
                340                 345                 350

Gly Arg Lys Ala Gln Asp Tyr Val Cys Gly Leu Pro Pro Arg Ile Arg
        355                 360                 365

Arg Leu Glu Glu Arg Ala Gln Gly Arg Ala Lys Gln Ala Pro Lys Ile
    370                 375                 380

Pro Phe Ser Trp Ile His Asp Arg Glu Val Gln Leu
385                 390                 395

<210> SEQ ID NO 43
<211> LENGTH: 393
<212> TYPE: PRT
<213> ORGANISM: Solanum commersonii

<400> SEQUENCE: 43

Met Ala Leu Asn Phe Asn Ser Pro Thr Phe Gln Ser Ile Lys Thr Thr
1               5                   10                  15

Arg Arg Pro Cys Ser Pro Leu Arg Ser Pro Arg Val Phe Met Ala Ser
            20                  25                  30

Thr Leu Arg Pro Pro Ser Val Glu Asp Gly Asn Val Lys Lys Pro Phe
        35                  40                  45

Ser Pro Pro Arg Glu Val His Val Gln Val Thr His Ser Met Pro Pro
    50                  55                  60

Glu Lys Arg Glu Ile Phe Asp Ser Leu His Gly Trp Ala Asp Asn Asn
65                  70                  75                  80

Ile Leu Gly His Leu Lys Pro Val Glu Lys Cys Trp Gln Ala Ser Asp
                85                  90                  95

Phe Leu Pro Asp Pro Ala Ser Glu Gly Phe Glu Asp Gln Val Lys Glu
            100                 105                 110

Leu Arg Glu Arg Cys Lys Glu Ile Pro Asp Asp Tyr Phe Val Val Leu
        115                 120                 125

Val Gly Asp Met Ile Thr Glu Glu Ala Leu Pro Thr Tyr Gln Thr Met
130                 135                 140

Leu Asn Thr Leu Asp Gly Val Arg Asp Glu Thr Gly Ala Ser Leu Thr
145                 150                 155                 160

Pro Trp Ala Ile Trp Thr Arg Ala Trp Thr Ala Glu Glu Asn Arg His
                165                 170                 175

Gly Asp Leu Leu Asn Lys Tyr Leu Tyr Leu Ser Gly Arg Val Asp Met
            180                 185                 190

Arg Gln Ile Glu Lys Thr Ile Gln Tyr Leu Ile Gly Ser Gly Met Asp
        195                 200                 205

Pro Arg Thr Glu Asn Asn Pro His Leu Gly Phe Ile Tyr Thr Ser Phe
    210                 215                 220

Gln Glu Arg Ala Thr Phe Ile Ser His Gly Asn Thr Ala Arg His Ala
225                 230                 235                 240

Lys Glu His Gly Asp Met Lys Leu Ala Gln Val Cys Gly Ile Ile Ala
                245                 250                 255

Ala Asp Glu Lys Arg His Glu Thr Ala Tyr Thr Lys Ile Val Glu Lys
            260                 265                 270

Leu Phe Glu Val Asp Pro Asp Gly Thr Val Leu Ala Val Ala Asp Met
        275                 280                 285
```

```
Met Arg Lys Lys Ile Ser Met Pro Ala His Leu Met Tyr Asp Gly Arg
    290                 295                 300

Asp Asp Asn Leu Phe Glu His Phe Ser Thr Val Ala Gln Arg Leu Gly
305                 310                 315                 320

Val Tyr Thr Ala Lys Asp Tyr Ala Asp Ile Leu Glu Phe Leu Val Gly
                325                 330                 335

Arg Trp Glu Ile Glu Lys Leu Thr Gly Leu Ser Gly Glu Gly His Lys
            340                 345                 350

Ala Arg Asp Tyr Val Cys Gly Leu Ala Pro Arg Ile Arg Lys Leu Glu
        355                 360                 365

Glu Arg Ala Gln Ala Arg Ala Lys Gln Lys Ala Pro Val Pro Phe Ser
    370                 375                 380

Trp Val Phe Gly Lys Asp Ile Lys Leu
385                 390

<210> SEQ ID NO 44
<211> LENGTH: 305
<212> TYPE: PRT
<213> ORGANISM: Arabidopsis thaliana

<400> SEQUENCE: 44

Met Ser Leu Ser Ala Ser Glu Lys Glu Asn Asn Lys Lys Met Ala
1               5                   10                  15

Ala Asp Lys Ala Glu Met Gly Arg Lys Lys Arg Ala Met Trp Glu Arg
                20                  25                  30

Lys Trp Lys Arg Leu Asp Ile Val Lys Ala Phe Ala Ser Leu Phe Val
            35                  40                  45

His Phe Leu Cys Leu Leu Ala Pro Phe Asn Phe Thr Trp Pro Ala Leu
        50                  55                  60

Arg Val Ala Leu Ile Val Tyr Thr Val Gly Gly Leu Gly Ile Thr Val
65                  70                  75                  80

Ser Tyr His Arg Asn Leu Ala His Arg Ser Phe Lys Val Pro Lys Trp
                85                  90                  95

Leu Glu Tyr Phe Phe Ala Tyr Cys Gly Leu Leu Ala Ile Gln Gly Asp
            100                 105                 110

Pro Ile Asp Trp Val Ser Thr His Arg Tyr His His Gln Phe Thr Asp
        115                 120                 125

Ser Asp Arg Asp Pro His Ser Pro Asn Glu Gly Phe Trp Phe Ser His
130                 135                 140

Leu Leu Trp Leu Phe Asp Thr Gly Tyr Leu Val Glu Lys Cys Gly Arg
145                 150                 155                 160

Arg Thr Asn Val Glu Asp Leu Lys Arg Gln Trp Tyr Tyr Lys Phe Leu
                165                 170                 175

Gln Arg Thr Val Leu Tyr His Ile Leu Thr Phe Gly Phe Leu Leu Tyr
            180                 185                 190

Tyr Phe Gly Gly Leu Ser Phe Leu Thr Trp Gly Met Gly Ile Gly Val
        195                 200                 205

Ala Met Glu His His Val Thr Cys Leu Ile Asn Ser Leu Cys His Val
    210                 215                 220

Trp Gly Ser Arg Thr Trp Lys Thr Asn Asp Thr Ser Arg Asn Val Trp
225                 230                 235                 240

Trp Leu Ser Val Phe Ser Phe Gly Glu Ser Trp His Asn Asn His His
                245                 250                 255

Ala Phe Glu Ser Ser Ala Arg Gln Gly Leu Glu Trp Trp Gln Ile Asp
```

-continued

```
                    260                 265                 270
Ile Ser Trp Tyr Ile Val Arg Phe Leu Glu Ile Gly Leu Ala Thr
            275                 280                 285

Asp Val Lys Leu Pro Ser Glu Ser Gln Arg Arg Arg Met Ala Met Val
        290                 295                 300

Arg
305
```